(12) United States Patent
del Nido et al.

(10) Patent No.: US 12,310,559 B2
(45) Date of Patent: May 27, 2025

(54) INSTRUMENT PORT WITH INTEGRATED IMAGING SYSTEM

(71) Applicant: Children's Medical Center Corporation, Boston, MA (US)

(72) Inventors: Pedro J. del Nido, Lexington, MA (US); Nikolay V. Vasilyev, Newton, MA (US)

(73) Assignee: Children's Medical Center Corporation, Boston, MA (US)

( * ) Notice: Subject to any disclaimer, the term of this patent is extended or adjusted under 35 U.S.C. 154(b) by 315 days.

(21) Appl. No.: 15/430,014

(22) Filed: Feb. 10, 2017

(65) Prior Publication Data

US 2017/0231477 A1   Aug. 17, 2017

Related U.S. Application Data

(60) Provisional application No. 62/294,587, filed on Feb. 12, 2016.

(51) Int. Cl.
| | | |
|---|---|---|
| *A61B 1/018* | (2006.01) | |
| *A61B 1/00* | (2006.01) | |
| *A61B 1/05* | (2006.01) | |
| *A61B 1/06* | (2006.01) | |
| *A61B 17/34* | (2006.01) | |

(Continued)

(52) U.S. Cl.
CPC .......... *A61B 1/018* (2013.01); *A61B 1/00089* (2013.01); *A61B 1/00137* (2013.01); *A61B 1/05* (2013.01); *A61B 1/0676* (2013.01); *A61B 17/3423* (2013.01); *A61B 1/0684* (2013.01); *A61B 2090/306* (2016.02); *A61B 90/361* (2016.02)

(58) Field of Classification Search
CPC ....... A61B 1/00096; A61B 1/05; A61B 1/053; A61B 1/00101; A61B 1/00105; A61B 1/00137
See application file for complete search history.

(56) References Cited

U.S. PATENT DOCUMENTS

| | | |
|---|---|---|
| 4,436,087 A | 3/1984 | Ouchi |
| 4,961,738 A | 10/1990 | Mackin et al. |

(Continued)

FOREIGN PATENT DOCUMENTS

| | | |
|---|---|---|
| EP | 1426072 | 10/2008 |
| EP | 2433551 | 3/2012 |

(Continued)

OTHER PUBLICATIONS

International Search Report and Written Opinion in International Application No. PCT/US17/17445, dated May 5, 2017, 16 pages.

(Continued)

*Primary Examiner* — Alexandra L Newton
(74) *Attorney, Agent, or Firm* — Fish & Richardson P.C.

(57) ABSTRACT

An instrument port for introducing an instrument into a surgical site includes a port body, a bulb disposed on the distal end of the port body, and a channel extending from a proximal end to a distal end of the instrument port. The channel includes an instrument channel defined in the port body and a bulb channel defined in the bulb. An imaging system is disposed at or near the distal end of the instrument port. The imaging system is fluidically isolated from the surgical site.

22 Claims, 14 Drawing Sheets

(51) Int. Cl.
*A61B 90/00* (2016.01)
*A61B 90/30* (2016.01)

(56) References Cited

U.S. PATENT DOCUMENTS

| | | | |
|---|---|---|---|
| 5,002,042 | A | 3/1991 | Okada |
| 5,025,778 | A | 6/1991 | Silverstein |
| 5,261,391 | A | 11/1993 | Inoue |
| 5,300,087 | A | 4/1994 | Knoepfler |
| 5,323,768 | A | 6/1994 | Saito et al. |
| 5,454,807 | A | 10/1995 | Lennox et al. |
| 5,632,782 | A | 5/1997 | Adair |
| 6,036,685 | A | 3/2000 | Mueller |
| 6,419,626 | B1 | 7/2002 | Yoon |
| 6,749,559 | B1 | 6/2004 | Kraas et al. |
| 6,752,755 | B2 | 6/2004 | Akiba |
| 6,953,431 | B2 | 10/2005 | Barthel |
| 7,442,167 | B2 | 10/2008 | Dunki-Jacobs et al. |
| 7,537,562 | B2 | 5/2009 | Takano |
| 7,914,444 | B2 | 3/2011 | Moriyama et al. |
| 8,133,239 | B2 | 3/2012 | Oz et al. |
| 8,425,407 | B2 | 4/2013 | Sato et al. |
| 8,491,631 | B2 | 7/2013 | Del Nido et al. |
| 8,926,502 | B2 | 1/2015 | Levy et al. |
| 9,402,531 | B2 * | 8/2016 | Chin ................ A61B 1/00087 |
| 9,451,875 | B2 | 9/2016 | Sigmon, Jr. |
| 9,459,442 | B2 | 10/2016 | Miller |
| 9,709,795 | B2 | 7/2017 | Miller |
| 2002/0068853 | A1 | 6/2002 | Adler |
| 2003/0093071 | A1 | 5/2003 | Hauck et al. |
| 2006/0084839 | A1 | 4/2006 | Mourlas et al. |
| 2006/0235457 | A1 | 10/2006 | Belson et al. |
| 2006/0264708 | A1 | 11/2006 | Horne, Jr. |
| 2007/0066869 | A1 | 3/2007 | Hoffman |
| 2007/0299468 | A1 | 12/2007 | Viola |
| 2008/0015445 | A1 | 1/2008 | Saadat |
| 2009/0048486 | A1 * | 2/2009 | Surti .................... A61B 1/0008 600/127 |
| 2009/0171373 | A1 | 7/2009 | Farritor et al. |
| 2009/0318759 | A1 * | 12/2009 | Jacobsen ............... A61B 1/051 600/116 |
| 2010/0286475 | A1 | 11/2010 | Robertson |
| 2011/0288372 | A1 | 11/2011 | Petersen |
| 2011/0295072 | A1 | 12/2011 | Boulais et al. |
| 2012/0209074 | A1 | 8/2012 | Titus |
| 2012/0232342 | A1 | 9/2012 | Reydel |
| 2014/0213847 | A1 | 7/2014 | Green et al. |
| 2014/0213848 | A1 | 7/2014 | Moskowitz et al. |
| 2014/0221749 | A1 | 8/2014 | Grant et al. |
| 2015/0065795 | A1 | 3/2015 | Titus |
| 2015/0313633 | A1 | 11/2015 | Gross et al. |
| 2015/0313634 | A1 * | 11/2015 | Gross .................... A61B 5/067 606/185 |
| 2015/0327754 | A1 | 11/2015 | Leeflang et al. |
| 2016/0367120 | A1 | 12/2016 | Dupont et al. |
| 2018/0098850 | A1 | 4/2018 | Rafiee et al. |

FOREIGN PATENT DOCUMENTS

| | | |
|---|---|---|
| JP | 3793368 B2 | 7/2006 |
| WO | WO 2003/101287 | 12/2003 |
| WO | WO 2010/083480 | 7/2010 |
| WO | WO 2011/047339 | 4/2011 |
| WO | WO 2014/112101 | 7/2014 |

OTHER PUBLICATIONS

International Search Report and Written Opinion in International Application No. PCT/US2016/038147, dated Sep. 8, 2016, 10 pages.
P. Dupont; "Invention Disclosure—Cardioscopes"; May 21, 2016; 5 pp.
International Preliminary Report on Patentability in International Application No. PCT/US2016/038147, dated Dec. 19, 2017, 9 pages.
Extended European Search Report in European Application No. 17750861.1, dated Sep. 30, 2019, 7 pages.
Ataollahi et al.; "Cardioscopic Tool-Delivery Instrument for Beating-Heart Surgery"; IEE/ASME Transactions on Mechatronics, vol. 21, No. 1, Feb. 2016; 7 pages.
Vasilyev et al.; "A Novel Cardioport for Beating-Heart Image-Guided Intracardiac Surgery"; Children's Hospital Boston, Harvard Medical School, Boston, Massachusetts Institute of Technology, Cambridge, Massachusetts; International Society for Minimally Invasive Cardiothoracic Surgery (ISMICS); Jun. 3, 2009; 17 pages.
International Preliminary Report on Patentability in International Application No. PCT/US2017/017446, dated Aug. 14, 2018, 9 pages.
Ahmed et al., "Initial clinical experience with a novel visualization and virtual electrode radiofrequency ablation catheter to treat atrial flutter," Heart Rhythm, Mar. 2011, 3: 362-367
Padala et al., Transapical beating heart cardioscopy technique for off-pump visualization of heart valves, The Journal of Thoracic and Cardiovascular Surgery, Jul. 2012,144: 231-234.
Shiose et al., "Cardioscopy-guided surgery: Intracardiac mitral and tricuspid valve repair under direct visualization in the beating heart," The Journal of Thoracic and Cardiovascular Surgery, Jul. 2011, 142: 199-202.
Uchida, "Recent Advances in Percutaneous Cardioscopy," Curr Cardiovasc Imaging Rep, 2011, 4: 317-327.
Vasilyev et al., "A novel cardioport for beating-heart, image-guided intracardiac surgery," The Journal of Thoracic and Cardiovascular Surgery, Dec. 2011, 142: 1545-1551.
Vasilyev et al., "Three-Dimensional Echo and Videocardioscopy-Guided Atrial Septal Defect Closure," Ann. Thorac. Surg., 2006, 82: 1322-6.
Bordignon et al., "Endoscopic ablation systems," Expert Review of Medical Devices, Mar. 1, 2013, 10(2):177-83.
EP Extended Search Report in European Appln. No. 22172564.1, dated Nov. 2, 2022, 8 pages.
CA Office Action in Canadian Appln. No. 3,014,320, mailed on Feb. 28, 2024, 4 pages.
EP Office Action in European Appln. No. 22172564.1, dated Jan. 31, 2024, 5 pages.
EP Office Action in European Appln. No. 17750861.1, mailed on Aug. 29, 2024, 3 pages.

* cited by examiner

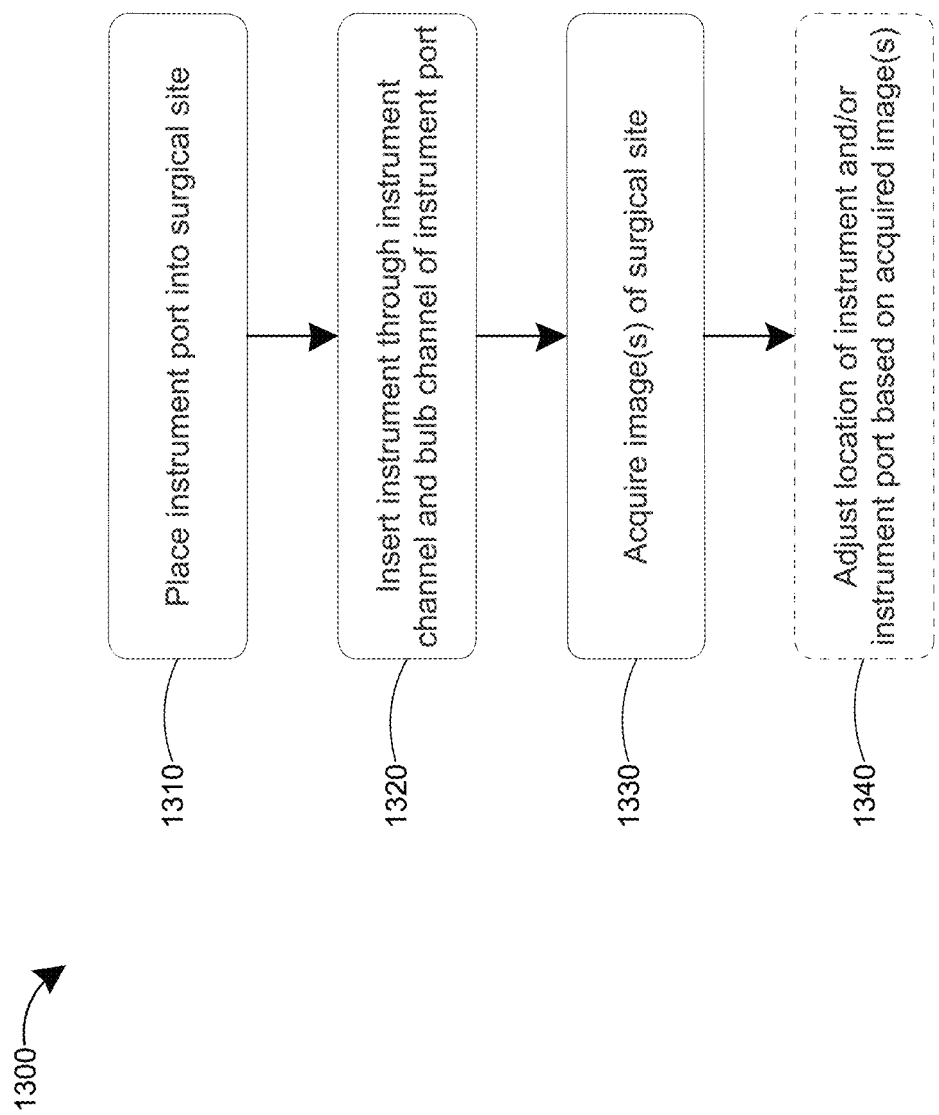

INSTRUMENT PORT WITH INTEGRATED IMAGING SYSTEM

CROSS-REFERENCE TO RELATED APPLICATIONS

This application claims the benefit of and priority to U.S. Provisional Application No. 62/294,587, entitled "Instrument Port With Integrated Imaging System," filed on Feb. 12, 2016, which is hereby incorporated by reference in its entirety.

STATEMENT REGARDING FEDERALLY-SPONSORED RESEARCH

This invention was made with government support under Grant nos. HL071128 and HL073647, awarded by The National Institutes of Health; and under Grant no. W81XWH-07-2-0001, awarded by the U.S. Department of the Army. The government has certain rights in the invention.

TECHNICAL FIELD

This application relates generally to devices and methods for minimally invasive image-guided surgery, such as cardiac surgery.

BACKGROUND

Instrument guides or ports can be used to guide the insertion of surgical instruments into a surgical site. As example of procedure where such instruments ports or guides are used is in beating-heart, minimally invasive cardiac procedures can be performed to repair heart defects or to treat vascular heart disease. To position an instrument port at an appropriate location near the surgical site, current systems rely on either the operator's vision or a secondary optical system, such as an endoscope, that is inserted next to or into the instrument guide.

Positioning an instrument using the operator's vision is limited to procedures where the surgical site is within the operator's line-of-sight, and thus cannot be used for most internal surgical sites. One problem with secondary optical systems is they requires a separate imaging channel in the instrument guide to receive the optical system (e.g., an endoscope). This causes the instrument guide to be larger in diameter and more expensive in order to accommodate the separate imaging channel. When the secondary optical system is located next to the instrument guide, it is exposed to the body fluids (e.g., blood) near the surgical site which limits the clarity, field of view, and/or depth of view of the secondary optical systems. When the secondary optical system contacts body fluids, it increases the risk of infection. This is compounded each time that the secondary optical system is introduced to the surgical site.

Current surgical imaging solutions are unable to function effectively in an environment containing body fluids or other biological or surgical debris, contaminants or obstructions. Such fluids and contaminants are generally not optically transparent and have other mechanical and optical characteristics that degrade the functioning of imaging systems during surgery, e.g., in the presence of blood at the aperture of the imaging system, lens or other optical components. This makes the imaging system useless or ineffective in such environments.

SUMMARY

The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Other objects, advantages and novel features of the disclosure will be set forth in the following detailed description of the disclosure when considered in conjunction with the drawings.

In an aspect, an instrument port for introducing an instrument into a surgical site includes a port body having an instrument channel extending from a proximal end to a distal end of the port body; a bulb disposed at the distal end of the port body, the bulb including a bulb channel extending from a proximal end to a distal end of the bulb, the bulb channel aligned with the instrument channel. The bulb channel and instrument channel are configured to receive the instrument; and an imaging system disposed at a distal end of the instrument port. The imaging system includes a camera and an illumination source, and the illumination source is configured to generate a light having a first wavelength. The bulb is at least partially optically transparent to the first wavelength of the light, and the imaging system is fluidically isolated from the surgical site. Such an optically-permissive bulb apparatus is designed in some aspects to displace blood and other surgical debris and contaminants, rendering the surgical site visible to an imaging and/or illuminating system used therewith.

In one or more embodiments, the illumination source includes a light guide configured to be optically coupled to a light source external to the instrument port. In one or more embodiments, the imaging system is fluidically isolated from the instrument channel and the bulb channel. In one or more embodiments, the bulb defines a hollow space within which the imaging system is disposed. The hollow space can extend inwardly from the proximal end of the bulb towards the distal end of the bulb. The imaging system can be disposed on a post that extends from the distal end of the instrument port, the hollow space configured to receive the post. In one or more embodiments, the imaging system is encapsulated in the bulb. In one or more embodiments, the hollow space is defined between a bulb wall and the distal end of the instrument port. In one or more embodiments, the hollow space is defined between a bulb wall and the distal end of the instrument port. The hollow space can be further defined by a bulb channel wall that defines the bulb channel.

In one or more embodiments, the imaging system is positioned such that a distal opening of the bulb channel falls within a field of view of the camera. In one or more embodiments, a shape or a material of the bulb is selected to reduce an optical distortion of an image, collected by the imaging system, of the surgical site. In one or more embodiments, the bulb is attached to the port body by a fluid-tight seal. In an aspect, the optical viewing or imaging capability of the present system is maximized, especially in a field of view proximal to a surgical site by the use of the presently-described bulb apparatus. For example, by making the bulb apparatus from an optical material of choice and/or shaping the profile of said bulb and/or processing images obtained through said bulb, it is possible to provide an operator with a useful view of the surgical procedure as seen through said bulb, including at a working end of a surgical tool.

In another aspect, a method for introducing an instrument into a surgical site includes placing an instrument port into the surgical site, wherein the instrument port comprises a port body and a bulb disposed at a distal end of the port body; inserting the instrument into a channel that extends from a distal end to a proximal end of the instrument port, the channel comprising an instrument channel extending through the port body and a bulb channel extending through the bulb; and acquiring an image of the surgical site using an imaging system disposed at a distal end of the instrument port, wherein the imaging system includes a camera and an illumination source, wherein the imaging system is fluidically isolated from the surgical site.

In one or more embodiments, the method further includes adjusting a location of the instrument based on the image acquired with the imaging system. The method can also include transmitting image data for the image to a computing system external to the instrument port. In one or more embodiments, the image data are transmitted wireless or via a data transmission component connected to the camera, the transmission component extending through the port body. The method can also include displaying the image on a display screen, the display screen in electrical communication with the computing system. In one or more embodiments, the method also includes generating, by the illumination source, a light having at least a first wavelength; and illuminating the surgical site with the light, wherein the bulb is at least partially optically transparent to the first wavelength of the light. In one or more embodiments, the illumination source comprises a light guide and the method further comprises coupling the light guide to a light source external to the instrument port.

Other features and advantages of the invention will be apparent from the following detailed description, from the drawings, and from the claims.

BRIEF DESCRIPTION OF THE DRAWINGS

For a fuller understanding of the nature and advantages of certain aspects of the invention, reference is made to the following detailed description of preferred embodiments and in connection with the accompanying drawings, in which:

FIG. 13 is a flow chart of a method for introducing an instrument into a surgical site.

DETAILED DESCRIPTION

This disclosure is based, at least in part, on the discovery that an imaging system can be integrated on or near the distal tip of an instrument port and fluidically isolated from the exterior of the instrument port in order to provide a compact instrument port with visualization capabilities. The instrument ports described herein can be used to assist in visualization of minimally invasive surgical procedures, such as image-guided cardiac procedures in beating or arrested hearts. A surgical instrument is inserted into an instrument channel extending through the instrument port. The positioning of the instrument port itself and the surgical instrument and the execution of the surgical procedure using the surgical instrument can be observed and guided based on images acquired by the distal imaging system. The imaging system, which includes a camera and an illumination source, is fluidically isolated from the instrument and from the surgical site by a bulb disposed at the distal end of the instrument port. The bulb can be at least partially optically transparent to a wavelength of light emitted by the illumination source.

Figure 1:
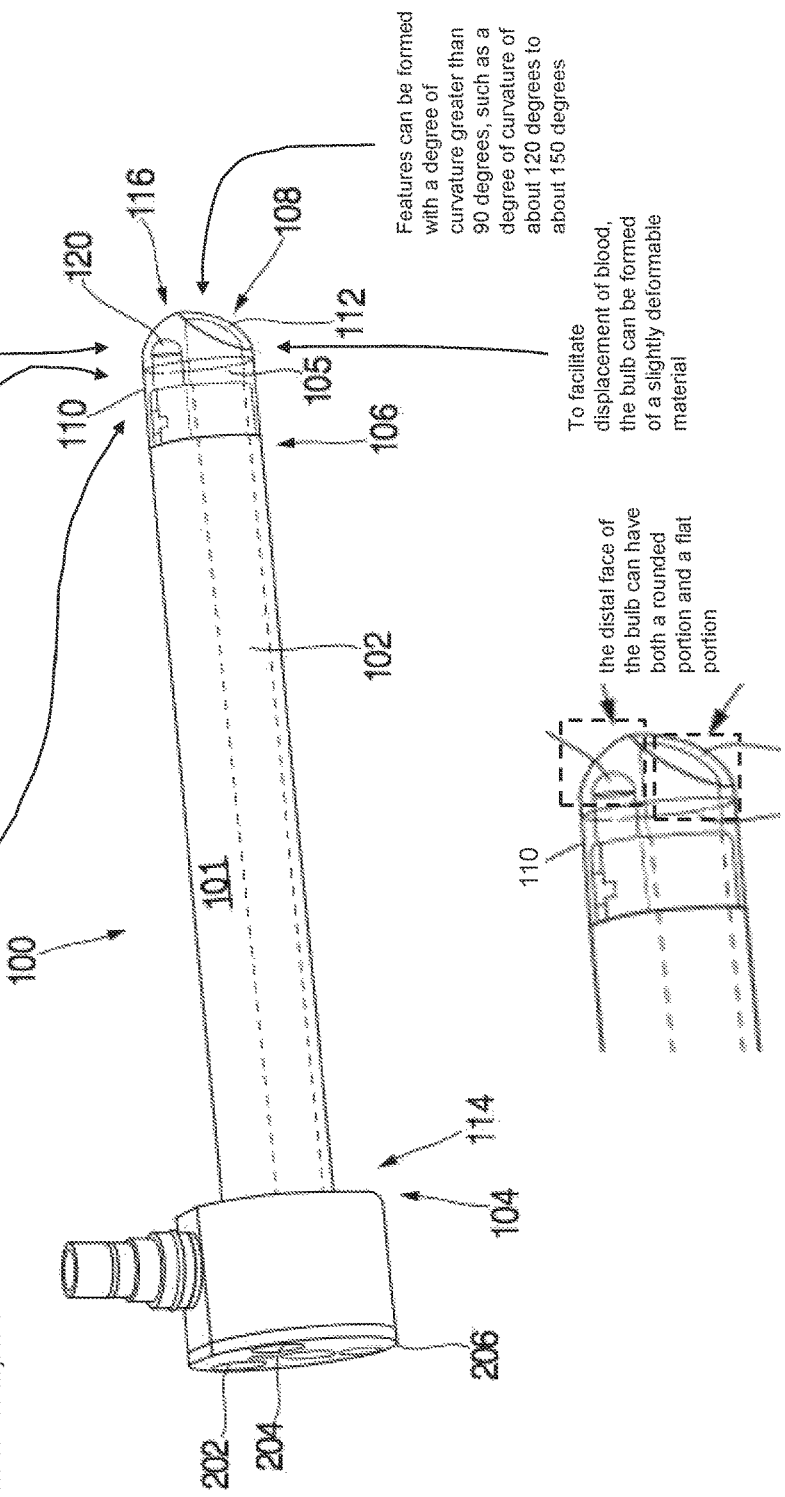
FIG. 1 is a perspective view of an instrument port for introducing one or more instruments into or near a surgical site of a patient according to one or more embodiments.

FIG. 1 is a perspective view of an instrument port 100 for introducing one or more instruments into or near a surgical site of a patient according to one or more embodiments. The instrument port 100 includes a port body 101, a bulb 110, and an imaging system 120. The port body 101 includes a housing that defines a hollow instrument channel 102 that extends from a proximal end 104 to a distal end 106 of the port body 101. The port body 101 can be formed from, or can include, a biocompatible material that is appropriate for use in surgical applications. For example, the port body 101 can be formed from, or can include, a medical grade polymer plastic, such as polyvinylide fluoride, polypropylene, polyacetal, polycarbonate, PolyEthylEthylKetone (PEEK), or another polymer; silicone; silicone rubber, or another material. In some examples, the port body 101 can be formed from a rigid or durable material, such as stainless steel, glass, PEEK, or another durable material, which can be sterilized for re-use. In some embodiments, the port body 101 includes a combination of two or more of any of the foregoing materials. In addition or in the alternative, the port body 101 can include different sections or segments. Each section or segment can include the same or different material (s) as the other sections or segments. For example, one segment can include PEEK and another section can include polycarbonate. The segments/sections can be joined with an adhesive, a screw, or other device, preferably to form a fluid-tight seal between adjacent segments/sections.

In some examples, the port body 101 can be constructed as a disposable component that is intended for a single-use application. In some examples, the port body 101 can be formed from, or can include, a material that is ultrasound visible, such as polyvinylidene fluoride or Kynar® polymer plastic, such that the position of the instrument port 100 in the body of the patient can be visualized by ultrasound imaging. In some examples, such as when the port body 101 is formed from a material that is not ultrasound visible, one or more ultrasound visible markers can be attached to or included on the port body 101 to enable visualization of the position of the instrument port 100 by ultrasound imaging.

In some examples, the port body 101 can be formed from or coated with a hydrophilic material, such as polyvinylidene fluoride (PVDF), P(VDF-trifluoroethylene), P(VDF-tetrafluoroethylene), polytetrafluoroethylene (PTFE), another hydrophilic material, or a combination of two or more of the foregoing, to facilitate flushing of air bubbles from the instrument channel 102.

The bulb 110 is disposed at the distal end 106 of the port body 101. A hollow bulb channel 105 extends through the bulb 110 from a proximal end (facing the distal end 106 of port body 101) to a distal end 108 of the bulb 110. The bulb channel 105 is aligned or substantially aligned with the instrument channel 102 formed through the instrument port 100. Thus, the instrument channel and bulb channel 105 form a continuous channel from the proximal end 114 to the distal end 116 of instrument port 100.

An imaging system 120, including a camera (e.g., a still or a video camera) and an illumination source, is disposed at or near the distal end 116 of instrument port 100. The imaging system 120 is positioned and arranged so that the camera can acquire images of the distal opening 112 of the bulb channel 105 and/or the surgical site. In some embodiments, the imaging system 120 is disposed at the distal end 106 of the port body 101, in which case the bulb 110 covers the imaging system 120 with a fluid-tight seal. The fluid-tight seal causes the imaging system 120 to be fluidically isolated from external fluids, such as body fluids near a surgical site. Alternatively, the imaging system 120 can be disposed within or integrated into the bulb 110, for example encapsulated in a hollow region within bulb 110, which fluidically isolates the imaging system 120. In another embodiment, the imaging system 120 is disposed on a base, such as a post or pedestal, that extends from the distal end of port body 101 into a hollow region defined in a proximal side of bulb 110 to receive the imaging system. The bulb 110 is attached to the port body 101 with a fluid-tight seal to fluidically isolate the imaging system in the hollow region defined in the proximal side of bulb 110.

The imaging system 120 is positioned (e.g., within the bulb 110) such that the opening 112 of the bulb channel 105 and at least a portion of the distal face 108 of the bulb fall within the field of view of the camera, thus enabling imaging of the surgical site, the instrument emerging from the bulb channel 105, and/or the interaction between the instrument and tissue or medical devices at the surgical site. The bulb 110 can be designed such that there are few or no obstructions blocking the field of view of the camera. The camera of the imaging system 120 can be set back from the distal face 108 of the bulb 110 by an amount approximately equal to the focal distance of the camera. The illumination source of the imaging system 120 can be positioned relative to the camera and to the distal face 108 of the bulb 110 such that the field of view of the camera is uniformly illuminated. Uniform illumination can help prevent the occurrence of shadows or dark spots that may limit the quality of the images acquired by the camera.

The imaging system 120 is fluidically isolated from the exterior of the instrument port 100 (e.g., from tissue and body fluids, such as blood, external to the instrument port 100), from the instrument channel 102 and bulb channel 105, and from the instrument inserted into the instrument channel 102 and bulb channel 105. When a component is fluidically isolated from a feature, there is no path for fluid communication between the component and the feature. Thus, the bulb 110 acts as an enclosure that fluidically isolates the components of the imaging system 120 from the exterior of the instrument port, from the instrument channel 102 and bulb channel 105, 205, and from the instrument. Fluidically isolating the components of the imaging system 120 helps to prevent electrical signals from the imaging system from being carried to the surgical site by tissue, blood, or the instrument, thus helping to avoid unintended electrical stimulation of the surgical site. Unintended electrical stimulation can be particularly dangerous in cardiac procedures, in which unintended stimulation of the heart muscle can give rise to arrhythmias in the patient. Thus, the fluidic isolation is not only beneficial, but can also be important to prevent adverse health effects to the patient. Fluidically isolating the components of the imaging system 120 can also reduce the risk of infection during surgery since by reducing the number of components exposed to the surgical area.

The bulb 110 can be designed to reduce internal reflection of light at its distal face 108, enabling the surgical site to be well illuminated. For instance, the bulb 110 can be formed of a material having a refractive index similar to that of air, blood, or tissue, such that internal reflections at the distal face 108 of the bulb 110 are reduced. Example materials of bulb 110 can include glass, clear crystal, resins such as acrylics or polyurethanes, or other materials with a refractive index sufficient to reduce internal reflections at the distal face 108 of the bulb 110. In addition or in the alternative, the relative angle between the distal face 108 of the bulb 110 and the direction of illumination from the illumination source can be set to reduce internal reflections at the distal face 108 of the bulb. In addition or in the alternative, internal reflections at the distal face 108 of the bulb can be reduced by the presence of an anti-reflective coating on the inner surface of the bulb.

To carry out a surgical procedure, with reference to FIG. 1, the instrument port 100 is inserted into a patient's tissue, such as into tissue of the patient's heart, through an incision in the patient's skin and tissue, such that the distal end 108 of the bulb 110 is positioned at or near the surgical site. The proximal end 104 of the instrument port 100 extends outside of the chest wall and incision site to enable an operator to manipulate the instrument port 100. The instrument port 100 can be anchored in place at the surgical site, such as by suturing the instrument port 100 to the patient's tissue. An instrument is inserted through the instrument channel 102 and the bulb channel 105, emerging from the distal opening 112 of the bulb channel 105 on the distal end 108 of the bulb 110. The instrument port 100 is positioned within the body of the patient such that the instrument can access the surgical site. The imaging system 120 is positioned to be able to acquire images of the instrument emerging from the opening 112 of the bulb channel 105, images of the surgical site, and/or images of the interaction between the instrument and the surgical site during the surgical procedure.

The instrument channel 102 and bulb channel 105 can be sized to accept standard instruments, such as dissectors, graspers, scissors, needle holders, fan retractors, cautery instruments, insufflation needles, forceps, or other types of instruments. For instance, the instrument channel 102 and the bulb channel 105 can each have a diameter of about 2 mm to about 6 mm, such as about 2 mm, about 3 mm, about 4 mm, about 5 mm, about 6 mm, or any value or range therebetween. As used herein, "about" means plus or minus 10% of the relevant value. In some examples, the instrument port 100 can include multiple instrument channels 102 and corresponding bulb channels 105 such that multiple surgical instruments can be inserted into the instrument port 100 simultaneously or sequentially. The multiple instrument channels and bulb channels can each have the same diameter or can each have different diameters. In general, each instrument channel 102 and corresponding bulb channel 105 (e.g., when there are multiple channels) has the same or about the same diameter.

The instrument port 100 can include a flushing system that removes emboli and debris, such as dust or other contaminants, from the instrument channel 102 and the bulb channel 105. Removing emboli and debris helps to prevent air bubbles and foreign material from entering the surgical site during use of the instrument port 100. For example, prior to heart surgery, the flushing system can remove emboli and debris from entering the patient's heart during use of the instrument port 100, thus helping to avoid an embolism. The flushing system can include a proximal inlet port 202 that is in fluid communication with the instrument channel 102; a one-way valve at or near the distal opening 108 of the bulb channel 105; a proximal outlet port 204 that is in fluid communication with the instrument channel 102; and a proximal end seal.

To flush the instrument port 100, the inlet port 202 is connected to a fluid supply line or reservoir, such as a saline source, and the outlet port 204 is connected to a suction source. When suction is applied to the outlet port 204 from the suction source, fluid is drawn through the inlet port 202 from the reservoir and into the instrument channel 102. The fluid flows through the instrument channel 102 and the bulb channel 105 in a gap between the inner walls of the channels 102, 105 and the instrument inserted therein. The fluid, carrying emboli and debris removed from the channels 102, 105, is withdrawn from the instrument port through the outlet port 204.

In an aspect, a constant negative pressure (e.g., from a surgical room vacuum port, pump, etc.) is provided and coupled to a suction port through said device to apply a relatively constant suction at the distal end thereof. In one instance, a manually or automatically operated valve or relay is used to actuate suction at regular intervals or as desired or according to some sensor indicating a need for said suction.

Other ports are further provided as needed, for example to run fiber optic or optical source conduits through said device, e.g., from a light source outside the device to a tip of a fiber proximal to its distal end 116 and/or within bulb 110. In an embodiment, a LED light source may be disposed within bulb volume 110 to forward illuminate a surgical work space. In another embodiment, a light source outside said apparatus is coupled to a light channel, wave guide or fiber so as to propagate light from said light source towards a distal end of said channel, guide or fiber to illuminate the work space.

As discussed, the flushing system can include a one-way valve that is disposed at or near the distal opening 108 of the bulb channel 105. The one-way valve opens responsive to a positive pressure applied to the valve from within the bulb channel 105, such as when pushed open during insertion of the instrument therethrough. During flushing of the instrument port, when a negative pressure (a suction) is applied to the one-way valve, the one-way valve remains closed, thus preventing emboli and debris carried by the flushing fluid from entering the patient's body. Additionally, this can prevent or reduce blood from the body from being drawn into the instrument channel by an applied suction. The one-way valve also remains closed when a positive pressure is applied to the valve from outside of the instrument port 100, such as when exposed to pressure in the heart, thus enabling the instrument port 100 to be used in high-pressure environments, such as in both atrial and ventricular applications, without aspiration of blood into the channels 102, 105 of the instrument port. In some examples, the one-way valve is a check valve, which is a compliant flexure that opens when pushed by the distal end of the instrument, remains sealed while the instrument is inserted therethrough, and seals when the instrument is removed. In some examples, the one-way valve is a tricuspid valve.

The proximal end seal can be a panel 206 removably attached to the instrument port 100, e.g., by a screw, a clip, or another attachment mechanism. A seal, such as an O-ring, a medical-grade adhesive, or another type of seal, can be disposed between the panel and the instrument port 100 to achieve a fluid-tight fit between the panel and the instrument port 100.

In some embodiments, the instrument is secured with a securing mechanism in the instrument channel 102 before being flushed by the flushing system. The securing mechanism can prevent the instrument from opening the one-way valve during flushing, for example by an inadvertent push on the proximal end of the instrument. Additional description of the flushing system can be found in U.S. application Ser. No. 13/792,916, the contents of which are incorporated herein by reference in their entirety.

Figure 2:
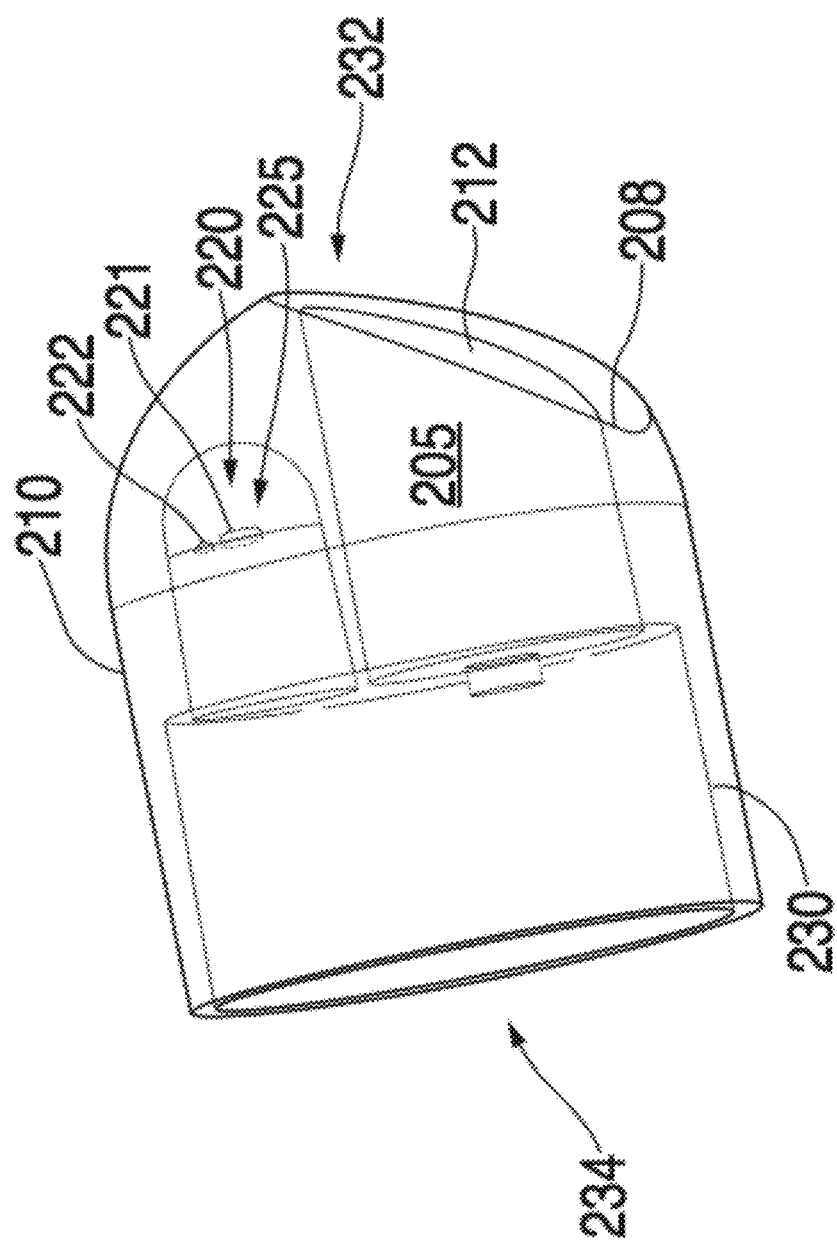
FIG. 2 is a detailed view of a bulb for an instrument port according to one or more embodiments.

FIG. 2 is a detailed view of a bulb 210 for an instrument port according to one or more embodiments. Bulb 210 can be the same or different than bulb 110 illustrated in FIG. 1. As shown in FIG. 2, the bulb 210 includes a collar 230, a bulb channel 205 and a hollow region 225 that at least partially encloses imaging system 220, including camera 221 and illumination source 222.

The camera 221 can be a high-resolution camera, such as a camera with millimeter-level resolution or sub-millimeter-level resolution. The camera 221 can be a complementary metal-oxide semiconductor (CMOS) camera, a charge-coupled device (CCD) camera, or another type of camera. The camera 221 can have a diameter of 5 mm or less. Example cameras include ⅛ Color CMOS CAMERA Module (Misumi Electronics Corp., Taiwan), Medigus Micro ScoutCam™ 1.2 system (Omer, Israel), and AWAIBA NanEye image sensor (CMOSIS AMERICA LLC, Raleigh, NC, USA). The camera 221 can capture still and/or moving images (e.g., as a video camera).

The illumination source 222 can emit visible light (e.g., white light or light of a specific wavelength or range of wavelengths), near-infrared light, and/or ultraviolet light. In some examples, the illumination source can emit visible light between 400 nm and 700 nm, infrared light between 1400 nm and 3000 nm, near infrared light between 700 nm and 1400 nm, and/or ultraviolet light between 280 nm and 400 nm. The illumination source 222 can include or can be optically coupled to (e.g., via a light guide) one or more light emitting diodes (LEDs) 304 capable of emitting the desired wavelength(s) or wavelength range(s).

The collar 230 is disposed on a proximal side 234 of the bulb 210 and is configured to engage with the distal end 106 of the port body 101. Thus, in some embodiments, collar 230 receives the distal end 106 of the port body 101 (i.e., collar 230 has a larger diameter (or other dimension if the components are not circular in cross section) than the distal end 106 of the port body 101). In other embodiments, the distal end 106 of the port body 101 receives the collar 230 (i.e., the distal end 106 of the port body 101 has a larger diameter (or other dimension if the components are not circular in cross section) than the collar 230). In either case, a fluid-tight seal is formed between the collar 230 and the distal end 106 of the port body 101.

The tip 232 of the bulb 210 is a solid or substantially solid housing with the bulb channel 205 and hollow region 225 defined therein. The imaging system 220 is disposed in the hollow region 225. In some embodiments, the camera 221 and illumination source 222 are disposed on a platform disposed in hollow region 225, which can be positioned and arranged so that the camera 221 can view the opening 212 of bulb channel 205, the surgical site, and/or the instrument as it interacts with the surgical site.

The tip 232 can provide an optically clear and/or substantially unimpeded optical path between the imaging system 220 and the surgical site. An unimpeded optical path is a path between the imaging system 220 and the surgical site having few or no obstacles obstructing the field of view of the imaging system 220 or distorting the images obtained by the imaging system 220. Unobstructed, undistorted images of the surgical site and of the interaction between the instrument and the surgical site can be valuable in assisting an operator of the instrument port in positioning the instrument port and the instrument, assessing the status of the surgical site, and performing surgical procedures using the instrument, while preventing tissue damage by the bulb or the surgical instrument.

The bulb 210 can be formed of a biocompatible material that is optically transparent to light used by the imaging system 220, such as visible light, infrared light, or ultraviolet light. An optically transparent material is a material that is at least partially transparent with respective to one or more wavelengths of light. For example, the bulb 210 can be formed of silicone, polycarbonate, polypropylene, polyacetal, polyether ether ketone (PEEK), or another material. In some embodiments, the lighting employed has wavelengths in the visible spectrum, for example between 400 nm and 700 nm. In other embodiments, illumination using infrared or near-infrared (IR) wavelengths, e.g., between 700 nm and 900 nm, or even up to 2000 nm may be used. In yet other embodiments, a quartz optical component is employed herein that permits ultra-violet illumination, e.g., using wavelengths between 250 nm and 400 nm. The bulb 210 can be fabricated by injection molding, casting, extrusion, three-dimensional (3-D) printing, or another fabrication process.

Blood is opaque to visible light (i.e., light with wavelengths in the range of 400 to 700 nm), and thus in the presence of blood, if the illumination source 222 uses visible light, the camera 221 would not able to image the surgical site. In some examples, during use, the instrument port 100 is positioned such that the distal face 208 of the bulb 210 comes into contact with tissue or a medical device (e.g., a patch) at the surgical site. The contact between the distal face 208 of the bulb 210 and the tissue or medical device at the surgical site displaces blood from between the distal face 208 of the bulb and the surgical site, creating a path between the imaging system 220 and the surgical site that is optically clear to visible light. To facilitate displacement of blood, the bulb 210 can be formed of a slightly deformable material, thus enabling the bulb 210 to conform to the shape of the tissue or medical device at the surgical site.

The shape of the distal face 208 of the bulb 210 can be selected based on characteristics of the surgical site where the instrument port 100 is to be used, e.g., based on characteristics of the tissue or medical device at the surgical site where the bulb 210 is to be used. In some examples, such as that shown in FIG. 2, the distal face 208 of the bulb 210 is rounded such that the bulb 210 has a hemispherical shape. A hemispherical bulb 210 with a rounded distal face 208 can be used, for instance, to contact soft tissue, such as in cardiac applications. In some examples, the distal face 208 of the bulb 210 can be flat, for instance, for use in contacting stiffer tissue such as muscle fascia, cartilage, bone, or in contacting soft tissue containing calcium deposition such as aortic or mitral valve annulus. In some examples, such as when the bulb 210 is to be used to contact multiple types of tissue with varying characteristics, the distal face 208 of the bulb 210 can have both a rounded portion and a flat portion.

A hemispherically-shaped bulb 210 with a rounded distal face 208 provides a similarly shaped contact surface between the distal face 208 of the bulb 210 and the tissue or medical device at the surgical site, regardless of the angle of approach of the instrument port 100 to the surgical site. The ability to operate the instrument port 100 at any arbitrary angle of approach can be beneficial in cardiac applications in which the angle of approach of the instrument port 100 to the surgical site is constrained. Trans-cardiac entry sites for the instrument port into the heart chambers can sometimes be limited by the location or conformation of the incision in the wall of the heart, constraining the angle of approach of the instrument port. A hemispherically shaped bulb 210 can provide a consistently shaped contact surface in such situations regardless of the constraints on the angle of approach of the instrument port 100. Those skilled in the art will further appreciate that spheroidal (or hemispheroidal) or similar profiles of the bulb 210 are possible, and may be adapted in size, diameter, cross-section or geometry to a given application. Some such examples are provided herein for the sake of illustration, but others are possible and are comprehended by the present disclosure and claims. For example, selected curvatures, flattened or contoured profiles and cross-sections of the bulb 210 or portions of the bulb 210 are within the scope of this disclosure and claims.

In some examples, when the imaging system 220 uses infrared light, imaging can be performed through blood, without a need for the bulb 210 to contact tissue or a medical device at the surgical site. Illumination with infrared light can enable imaging of structures ahead of the distal face 208 of the bulb 210. For instance, imaging with infrared light can enable imaging of tissue through blood at a distance of up to about 1.5 cm away from the tissue. Infrared imaging can be used, for instance, to guide placement of the instrument port within the heart of a patient or to visualize sensitive tissue at a surgical site prior to engaging a surgical instrument to manipulate tissue at the surgical site. In some examples, the imaging system 220 can use a light having a plurality of wavelengths, for example in the infrared spectrum and in the visible spectrum.

In some examples, one or more wires are connected to the camera 221 and the illumination source 222 (e.g., LEDs or the light guide 550, described below) to provide power to the camera 221, to provide power or light to the illumination source 222, and/or to transmit data collected by the camera 221 to a computing device or display screen. The wires can be embedded in a wall of the instrument port 100 (e.g., a wall of the port body 101) or they can be contained in a sealed, fluid-tight package that is threaded through another channel of the instrument port. In some examples, the camera 221 and the illumination source 222 are powered by a battery (not shown) housed at or near the distal end 106 of the port body 101, or housed in the bulb 210. In some examples, the camera 221 and the illumination source 222 are configured for wireless power transmission, wireless data transmission, or both. The data collected by the camera 221 can be transmitted in real time (e.g., with little or no delay between acquisition and transmission) for viewing by the operator of the instrument port 100 such that the operator can conduct the surgical procedure with guidance from the images.

The integration of the imaging system 120, 220 into the bulb 110, 210 allows the instrument port 100 to be constructed without a separate imaging channel, e.g., without an imaging channel for an endoscope. An instrument port without a separate imaging channel (such as the instrument port 100) can be more compact (e.g., can have a smaller diameter) than an instrument port with such a channel, which makes the instrument port 100 more ergonomic for the surgeon and less invasive for the patient.

Figure 3:
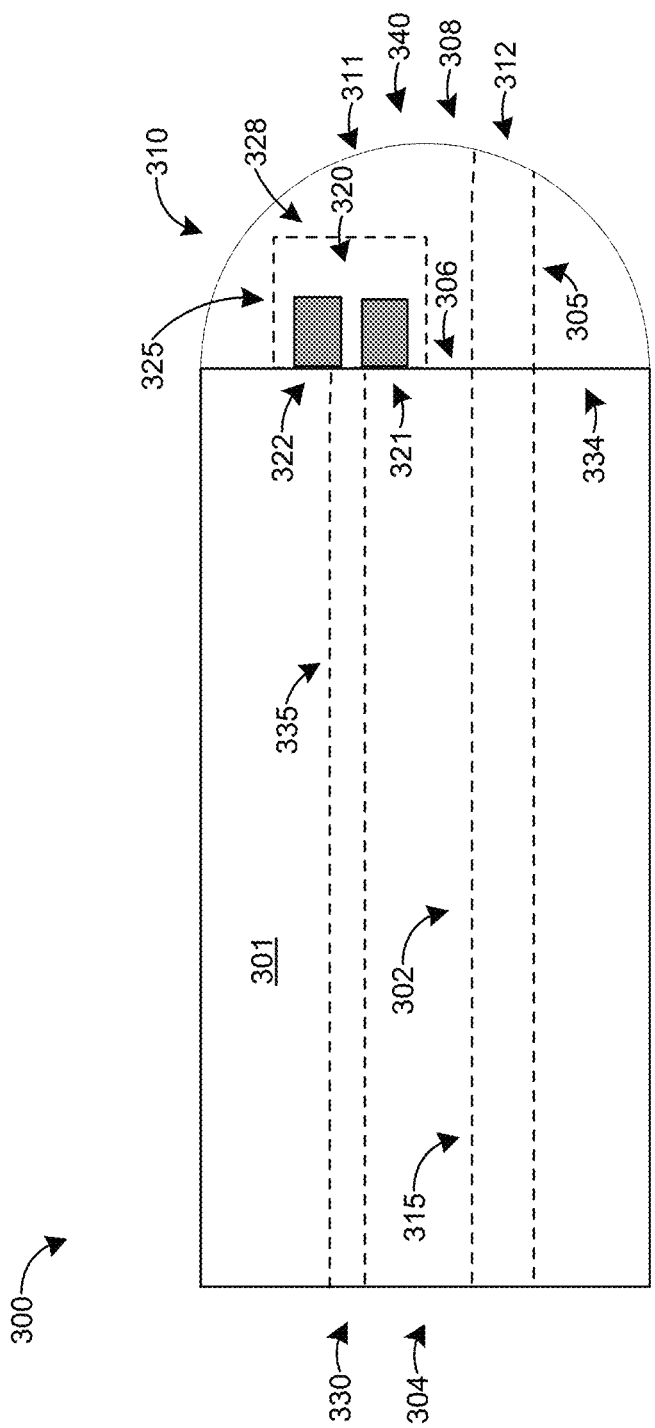
FIG. 3 is a simplified side view of an instrument port according to one or more embodiments.

FIG. 3 is a simplified side view of an instrument port 300 according to one or more embodiments. The instrument port 300 includes a port body or first housing 301 (in general, port body 301), a bulb or second housing 310 (in general, bulb 310), and a first channel 315 that extends from a proximal end 330 to a distal end 340 of the instrument port 300. The first channel 315 includes an instrument channel 302 defined in the port body 301 and a bulb channel 315 defined in the bulb 310. The instrument channel 302 extends from a proximal end 304 to a distal end 306 of the port body 301. The bulb channel 315 extends from a proximal end 334 to a distal end 308 of the bulb 310.

An imaging system 320, comprising a camera 321 and an illumination source 322, is disposed at the distal end 306 of the port body 301. The camera 321 and/or the illumination source 322 can be connected to an external component (e.g., a computer) and/or can receive power through wired connections that pass through an optional second channel 335 defined in the port body 301. The connection to the external component and/or the power can also be provided wirelessly. The imaging system 320 can be secured to the distal end 308 of port body 301 by an adhesive, a press-fit connection, a screw connection, and/or another type of connection, or a combination of two of more of the foregoing. In some embodiments, the imaging system 320 is the same or similar to the imaging system 120, 220 described above.

The camera 321 and/or the illumination source 322 can, for example, be connected to one or more outside components (e.g., a computer, a power source, a light source, etc.) along optional second channel 335 by one or more wires or cables that extend outside of the hollow region 325. Alternatively, the camera 321 and/or the illumination source 322 can be wirelessly powered and/or in wireless communication with the outside component(s). In some embodiments, one or more batteries for the imaging system 320 are disposed in the hollow space 320.

The imaging system 320 is covered by the bulb 310, which forms a fluid-tight connection with the port body 301. The imaging system 320 is enclosed in a hollow space 325 defined in the proximal end 334 of the bulb 310. In some embodiments, the imaging system 320 is set back or inset by a distance from a bulb wall 328 that defines the hollow space 325. In addition or in the alternative, the imaging system 320 can be inset from the external surface 311 of the bulb 310. This can reduce the possibility of fluid leakage or electrical coupling between the imaging wall 320 and the exterior of the bulb 310. For instance, the imaging system 320 can be inset from the external surface 311 of the bulb by a distance of at least about 0.5 mm, such as 0.5 mm, 0.75 mm, 1.0 mm, 1.25 mm, 1.5 mm, another distance, or any value or range between any two of the foregoing values. The desire for a large separation between the imaging system 320 and the bulb channel 305 and between the imaging system 120 and the external surface 311 of the bulb 310 can be balanced with the desire for an instrument port 300 with a small size and diameter.

The fluid-tight seal between the bulb 310 and the port body 301 helps to prevent fluid from reaching the imaging system 320 and helps prevent electrical signals from the imaging system from reaching tissue, blood, or the instrument. Examples of the fluid-tight seal between the bulb 310 and the port body 301 include a pressure-fit seal, a medical grade adhesive, an O-ring attachment, and/or another type of sealing mechanism, or combination of two or more of the foregoing. The seal can be constructed to withstand the fluid pressure present in the chambers of the heart, such as pressures of up to 150 mmHg or pressures as low as 3 mmHg. Some embodiments permit operation, especially during transients, in a pressure range up to 220 mmHg or as low as −5 mmHg. Using the fluid tight-seal, the bulb 310 can be removably attached to the port body 301 or the bulb 310 can be permanently attached to the port body 301.

The port body 301 and the bulb 310 can be formed out of the same or similar materials as the port body 101 and bulb 110, 210 described above. For example, the bulb 310 can be formed out of a material that is at least partially optically transparent to a wavelength of light emitted from illumination source 322.

Figure 4A:
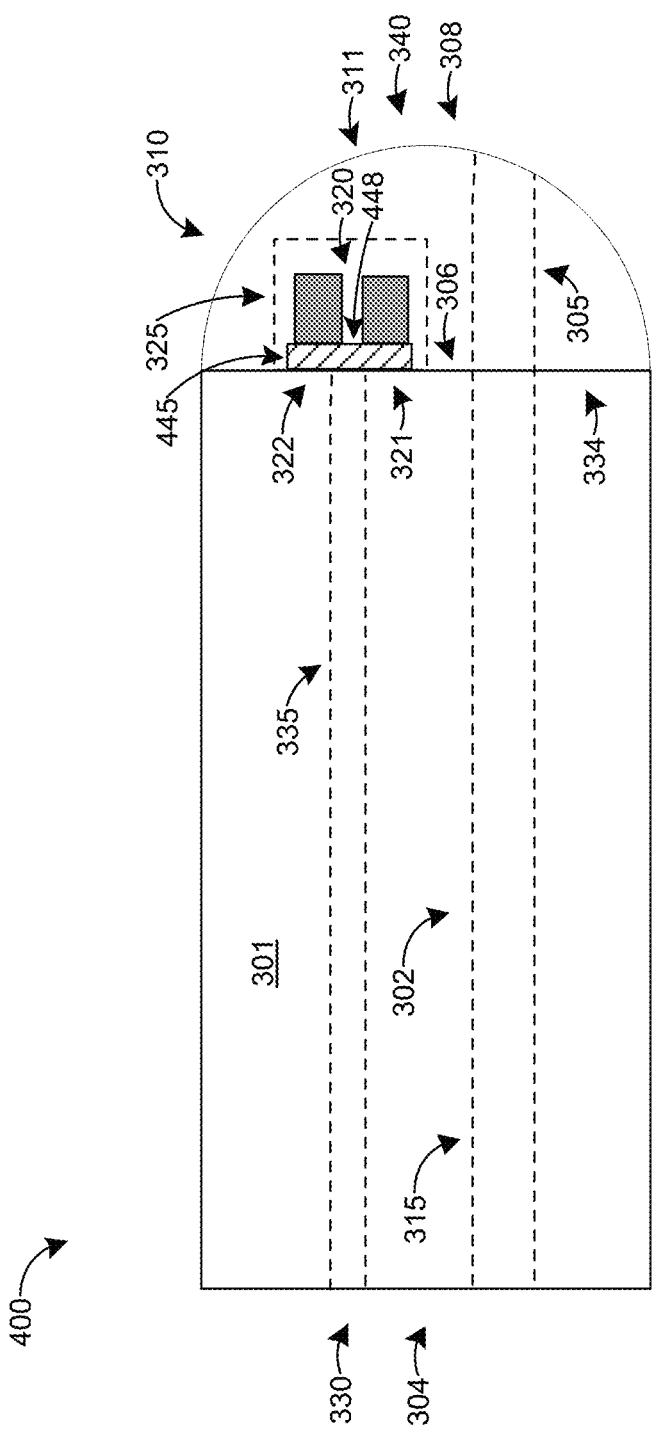
FIGS. 4A and 4B are simplified side views of an instrument port according to one more embodiments.
Figure 4B:
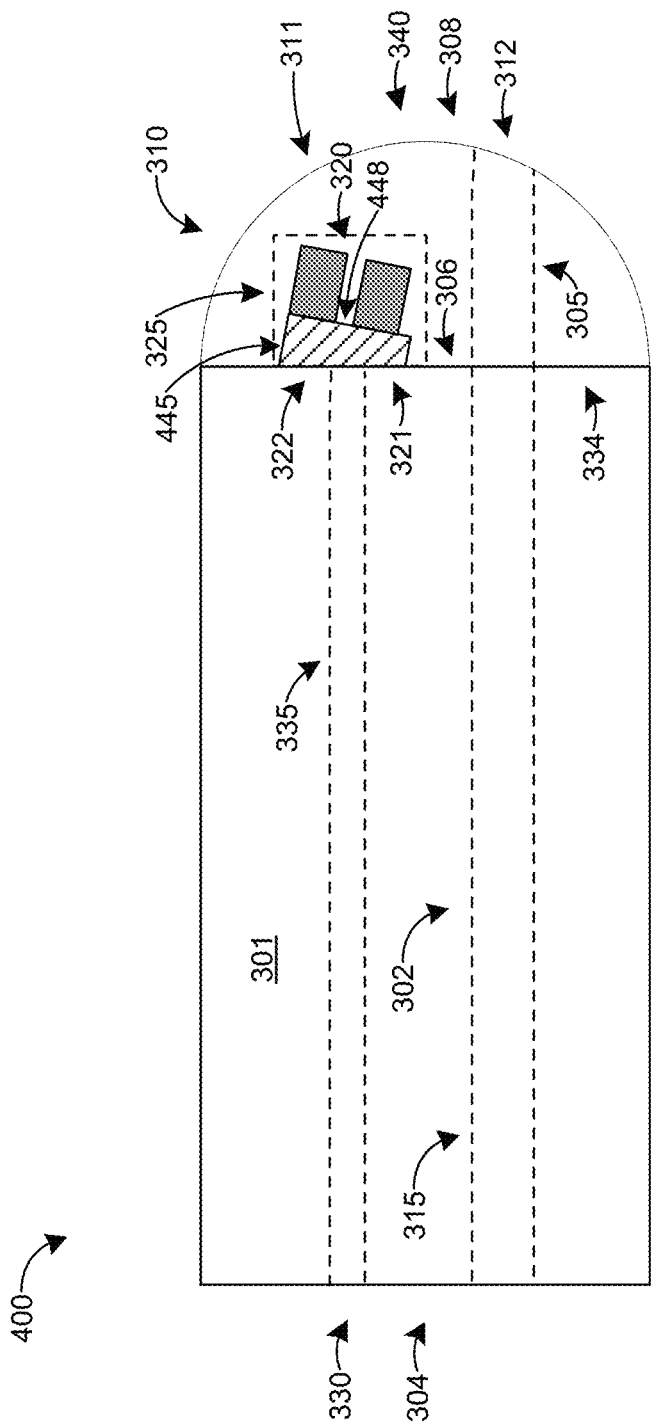

FIGS. 4A and 4B are simplified side views of an instrument port 400 according to one more embodiments. The instrument port 400 is the same or substantially the same as instrument port 300 but with the addition of an imaging support body 445. The imaging support body 445 is disposed on the distal end 306 of the port body 301. In the embodiment of FIG. 4A, the imaging support body 445 has a substantially equal cross-section width (i.e., the distance from the distal end 306 of the port body 301 to the distal face 448 of the imaging support body 445 is equal in the cross section illustrated in FIG. 4A).

As illustrated in FIGS. 4A and 4B, the camera 321 and illumination source 322 are disposed on the distal face 448 of the imaging support body 445. However, in other embodiments, only one of the camera 321 or the illumination source 322 is disposed on the imaging support body 445. The component of the imaging system 320 that is not disposed on the imaging support body can be disposed on the distal end 306 of the port body 301 or can be encapsulated in bulb 310. Alternatively, each component of the imaging system 320 is disposed on a separate imaging support body, each imaging support body having the same or different size as the other imaging support body. For example, the illumination source 322 can be disposed on an imaging support body that is "wider" than the imaging support body on which the camera 321 is disposed, e.g., that extends further distally than the support body on which the camera 321 is disposed. The "wider" imaging support body places the illumination source further towards the distal end 340 of the instrument port 400, which can allow light from the illumination source 322 to pass at advantageous angles around the camera 321 (and other imaging support body), for example to avoid shadowing of the surgical site and/or of the outlet 312 of the first channel 315.

FIG. 4B illustrates an embodiment where the imaging support body 445 has a variable cross sectional-width to angle the distal face 448 towards the outlet 312 of the first channel 315. The angled distal face 448 can reduce shadowing of the surgical site and/or of the outlet 312 of the first channel 315 by elevating the illumination source 322 towards the outlet 312 of the first channel 315. The illumination source 322 and the camera 321 are angled toward the outlet of the first channel 315, with the illumination source 322 extending further distally than the camera 321 such that shadowing of the surgical site and/or the outlet 312 by the camera 321 can be avoided. In some embodiments, the angle of distal face 448 can be adjusted by an actuator other adjustment mechanism in electrical communication with an external device, such as a computer, via a wired or wireless connection. The actuator can rotate the imaging support body 445 towards or away from the outlet 312 of the first channel 315, for example to view the area around the surgical site. In addition or in the alternative, the position or orientation of the camera 321 and/or the illumination source 322 can be adjusted using a shared or separate actuator(s) or other adjustment mechanism(s).

The integration of the imaging system 320 at or near the distal end 308 of the instrument port 300, 400 (e.g., at or on the distal end 306 of the port body 301, as illustrated in FIGS. 3, 4A, and 4B) allows the instrument port 300, 400 to be constructed without a separate imaging channel, e.g., without an imaging channel for an endoscope. An instrument port without a separate imaging channel (such as the instrument port 300, 400) can be more compact (e.g., can have a smaller diameter) than an instrument port with such a channel, which makes the instrument port 300, 400 more ergonomic for the surgeon and less invasive for the patient.

Figure 5:
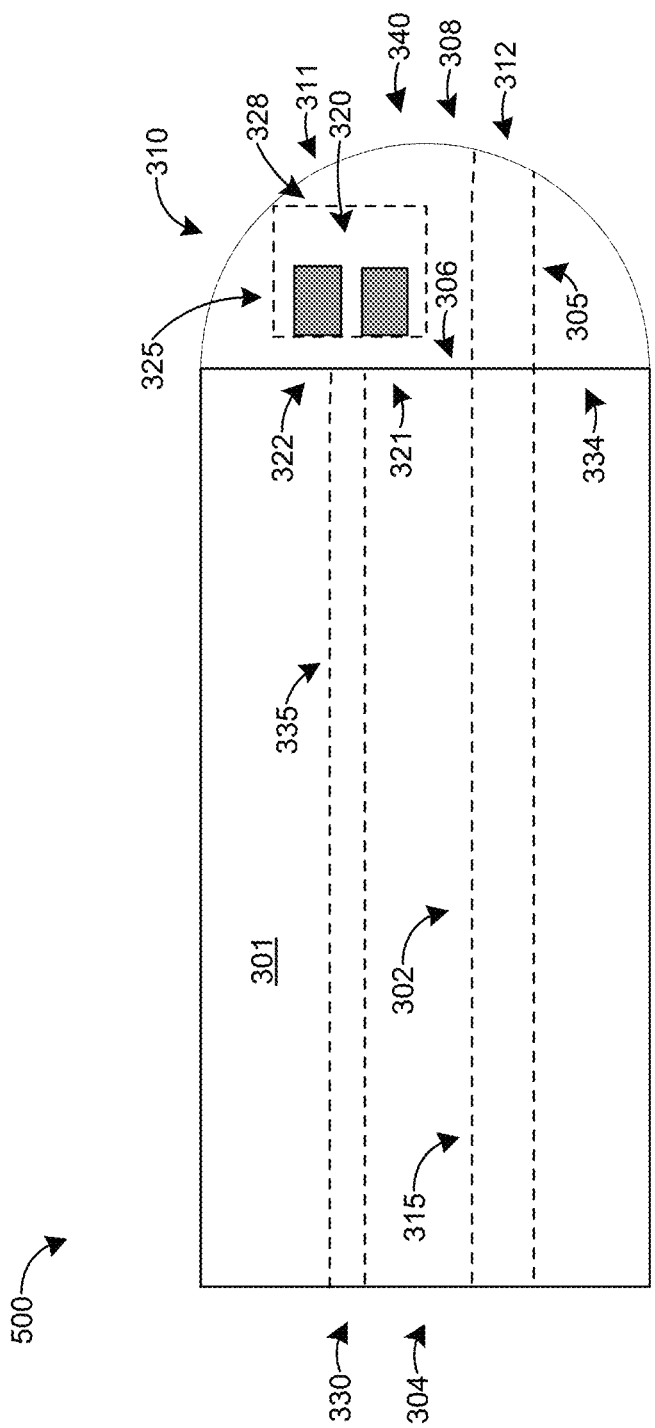
FIG. 5 is a simplified side view of an instrument port according to one or more embodiments.

FIG. 5 is a simplified side view of an instrument port 500 according to one or more embodiments. Instrument port 500 is the same or substantially the same as instrument port 300 but with a modification that the imaging system 320 is fully disposed and secured in the hollow region 325 defined in the bulb 310. As such, the hollow region 325 encloses and/or encapsulates the camera 321 and illumination source 322 of imaging system 320 in the bulb 310. In an alternative embodiment, the bulb 310 is formed around the imaging system 320 such that the components of the imaging system 320 (e.g., camera 321 and illumination source 322) are encapsulated within the material of the bulb. For instance, the bulb 310 can be casted or molded around the imaging system 320.

As described above, the camera 321 and/or the illumination source 322 can be connected to one or more wires or cables that extend outside of the hollow region 325, for example to one or more outside components (e.g., a computer, a power source, a light source, etc.) along optional second channel 335. Alternatively, the camera 321 and/or the illumination source 322 can be wirelessly powered and/or in wireless communication with the outside component(s). In some embodiments, one or more batteries for the imaging system 320 are disposed in the hollow space 320.

Figure 6:
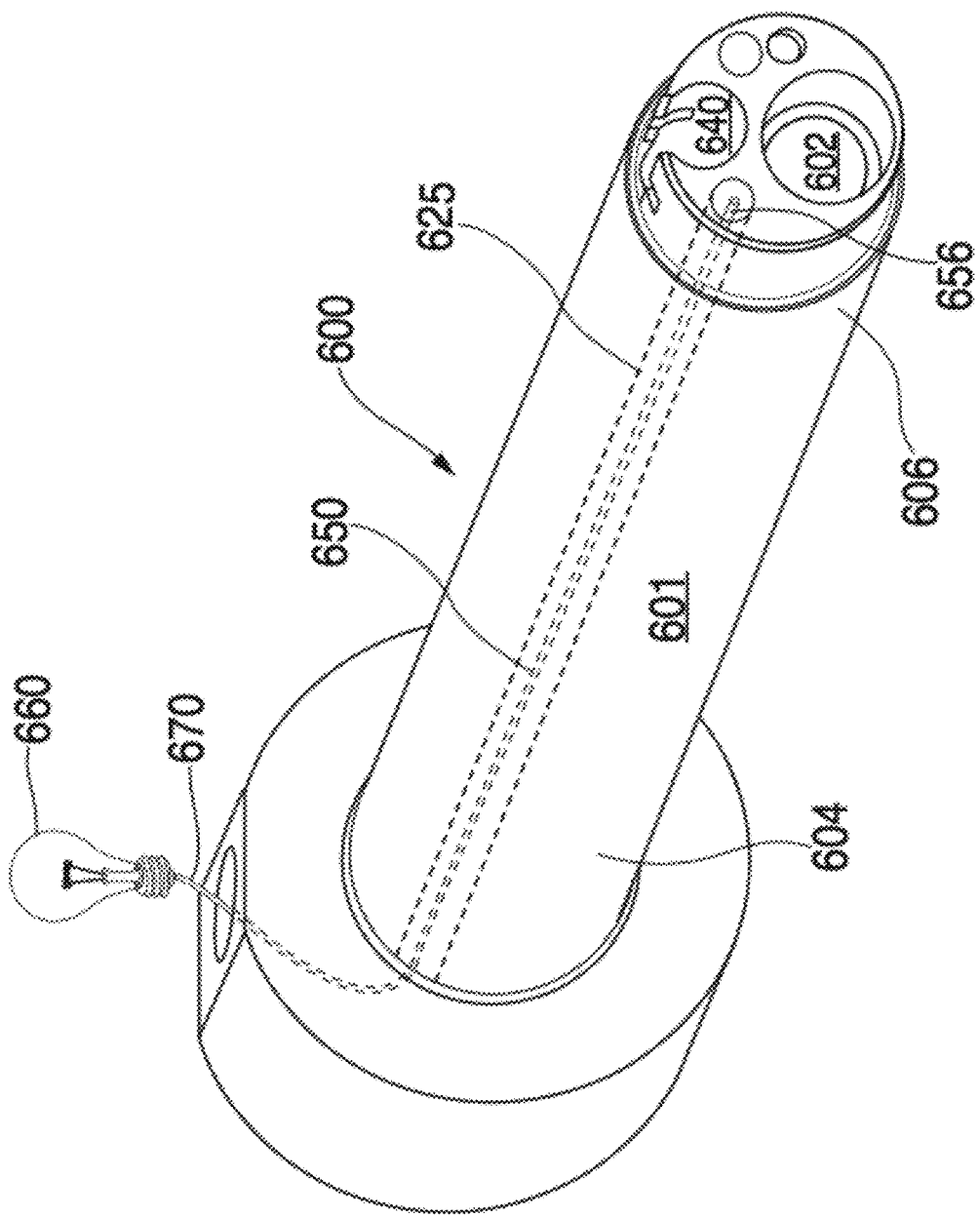
FIG. 6 is a perspective view of a port body according to one or more embodiments.

FIG. 6 is a perspective view of a port body 601 according to one or more embodiments. The port body 601 includes a light guide 650 that extends from a proximal end 604 to a distal end 606 of the port body 601. The light guide 650 can include an optical fiber cable, such an optical fiber cable made of glass, quartz, and/or plastic. In some embodiments, the light guide 650 is a fiber optic light guide cable, such as 495 Series cable available from KARL STORZ GmbH & Co., Tuttlingen, Germany. The light guide 650 (e.g., the optical fiber cable) can be embedded in a wall of the port body 601 or it can be inserted into an optional light guide channel 625 defined in the port body 601. The light guide channel 625 can be parallel to instrument channel 602 or they can be disposed an angle with respect each other.

At the proximal end 604 of the port body 601, the light guide 650 is optically coupled to an external light source 660, such as a lamp, laser, or LED. The lamp can be, in some embodiments, a standard endoscopy light source that is readily available in most surgical environments. The light guide 650 is coupled to the external light source 660 via a cable 670. In addition or in the alternative, the light guide 650 is coupled to the external light source 660 via a fiber coupler incorporated into the proximal end 604 of the port body 601. The light guide 650 is configured to carry light along its length and to emit light at least from its distal tip 656 as the illumination source described above. In FIG. 6, the distal tip 656 of the light guide 650 is disposed at the distal end 606 of the port body 601 near camera 640. Alternatively, the distal tip 656 of light guide 650 and camera 640 can be located in the bulb, as discussed above. In some examples, the light guide 650 is configured to emit light both along its length and at its distal tip 656.

Figure 7:
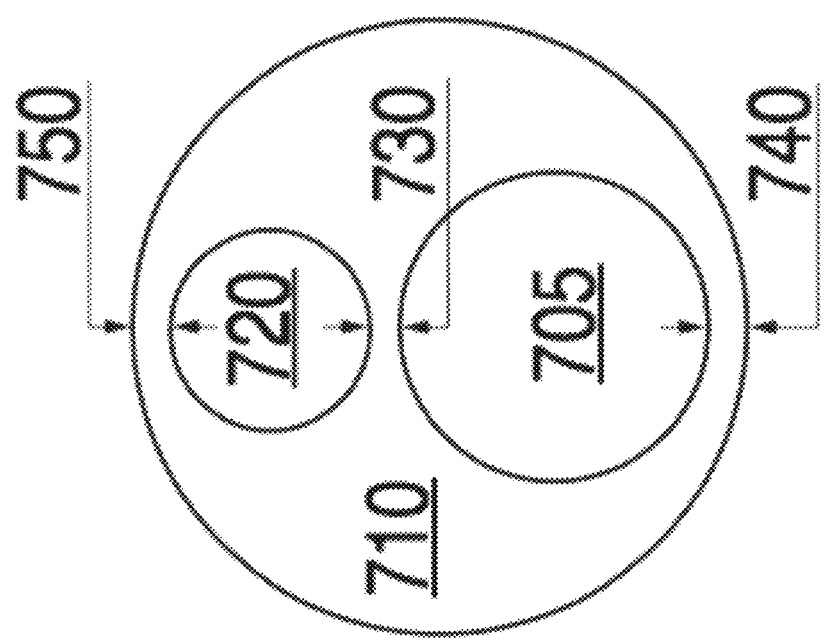
FIG. 7 is a cross-sectional view of a distal section of an instrument port that includes an imaging system according to one or more embodiments.

The instrument ports, as described above, can be made more compact by utilizing small-sized components for the imaging system 120, 220, 320 such as a small camera 221, 321 and a small illumination source 222, 322. FIG. 7 is a cross-sectional view of a distal section 710 of an instrument port that includes an imaging system camera according to one or more embodiments. For example, the cross-sectional view can be through the bulb or through the distal end of the port body, depending on the location of the camera. As illustrated in FIG. 7, the imaging system 720 is positioned proximal to the instrument channel or bulb channel 705. The instrument or bulb channel 705 and imaging system 720 can be the corresponding components from the instruments ports described herein. For example, instrument or bulb channel 705 can be the same as or similar to the instrument channels (e.g., instrument channel 102, 302) and/or the bulb channels described herein (e.g., bulb channel 105, 205 305). In addition, imaging system 720 can be the same as or similar to the imaging systems described herein (e.g., imaging system 120, 220, 320). The imaging system 720 and the instrument channel or bulb channel 705 (or both the instrument channel and the bulb channel) are separated by a lateral separation 730 to reduce the possibility of fluid leakage or electrical coupling (e.g., by direct electrical contact or capacitive coupling) between the imaging system 720 and (a) the instrument channel or bulb channel 705 and/or (b) the instrument inserted therein. For instance, the lateral separation 730 can be at least about 0.1 mm, such as from about 0.1 mm to about 0.5 mm, such as about 0.1 mm, 0.2 mm, 0.25 mm, 0.3 mm, 0.4 mm, 0.5 mm, another separation, or any value or range between any two of the foregoing values.

The size (e.g., diameter) of the imaging system 720, the size (e.g., diameter) of the instrument channel or bulb channel 705, and the lateral separation 730 together dictate the minimum acceptable diameter of the distal section 710 of the instrument port, and thus the diameter of instrument port (if the instrument port has a uniform diameter). In other embodiments, the instrument port can have a non-uniform diameter, for example to provide ergonomic or grip features on the outside of the instrument port. However, the instrument port can preferably have a diameter of at least the minimum acceptable diameter. The minimum acceptable diameter is also determined by the thickness 740, 750 of the respective walls between (a) the instrument channel or bulb channel 705 and the outer surface of distal section 710 and (b) the imaging system 720 and the outer surface of distal section 710, as illustrated in FIG. 7.

For a given instrument size (and hence instrument channel or bulb channel 705 diameter), the minimum acceptable diameter of the distal section 710 of the instrument port can be reduced by selecting smaller components for the imaging system 720. For instance, the camera of imaging system 720 can be a CMOS camera with a sensor having a width of less than about 8 mm, less than about 7 mm, less than about 6 mm, less than about 5 mm, less than about 4 mm, less than about 3 mm, less than about 2 mm, or any value or range therebetween. The illumination source can include one or more LEDs each having a diameter of less than about 5 mm, less than about 4 mm, less than about 3 mm, less than about 2 mm, less than about 1 mm, or any value or range therebetween.

Figure 8:
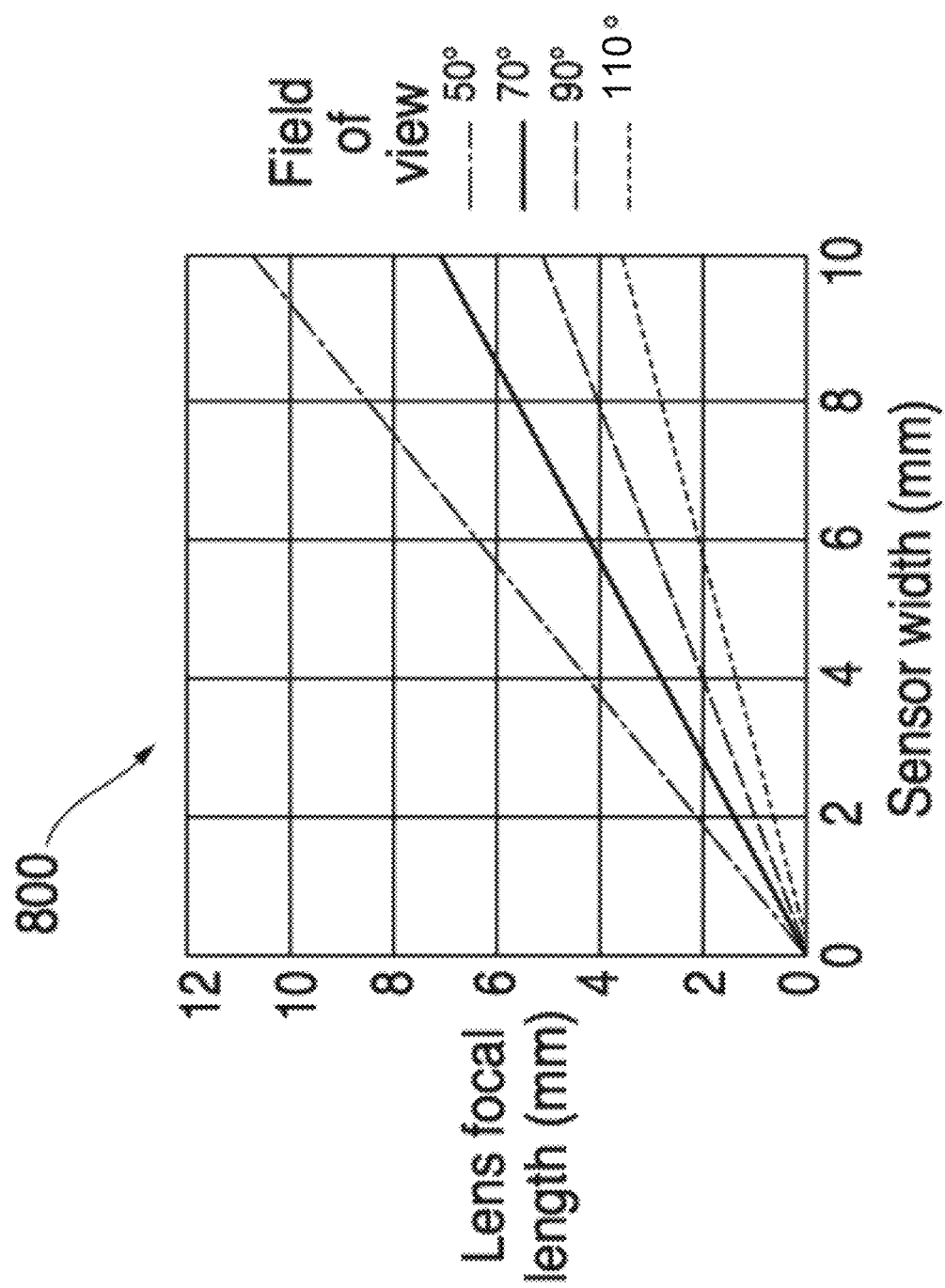
FIG. 8 is a representative plot of lens focal length versus sensor width for cameras with various fields of view.

The size of the camera (e.g., the width of the sensor of the camera) can be balanced against performance parameters of the camera, such as field of view, brightness, resolution, pixel size, f-number (sometimes referred to as relative aperture), or other parameters. FIG. 8 is a representative plot 800 of lens focal length versus sensor width for cameras with various fields of view. FIG. 8 illustrates that the field of view of a camera with a small sensor is smaller than the field of view for a camera with a larger sensor for a given focal length. For example, using a focal length of 4 mm, a sensor that is 4 mm wide has about a 5-degree field of view while a sensor that is 8 mm has about a 90-degree field of view.

Figure 9:
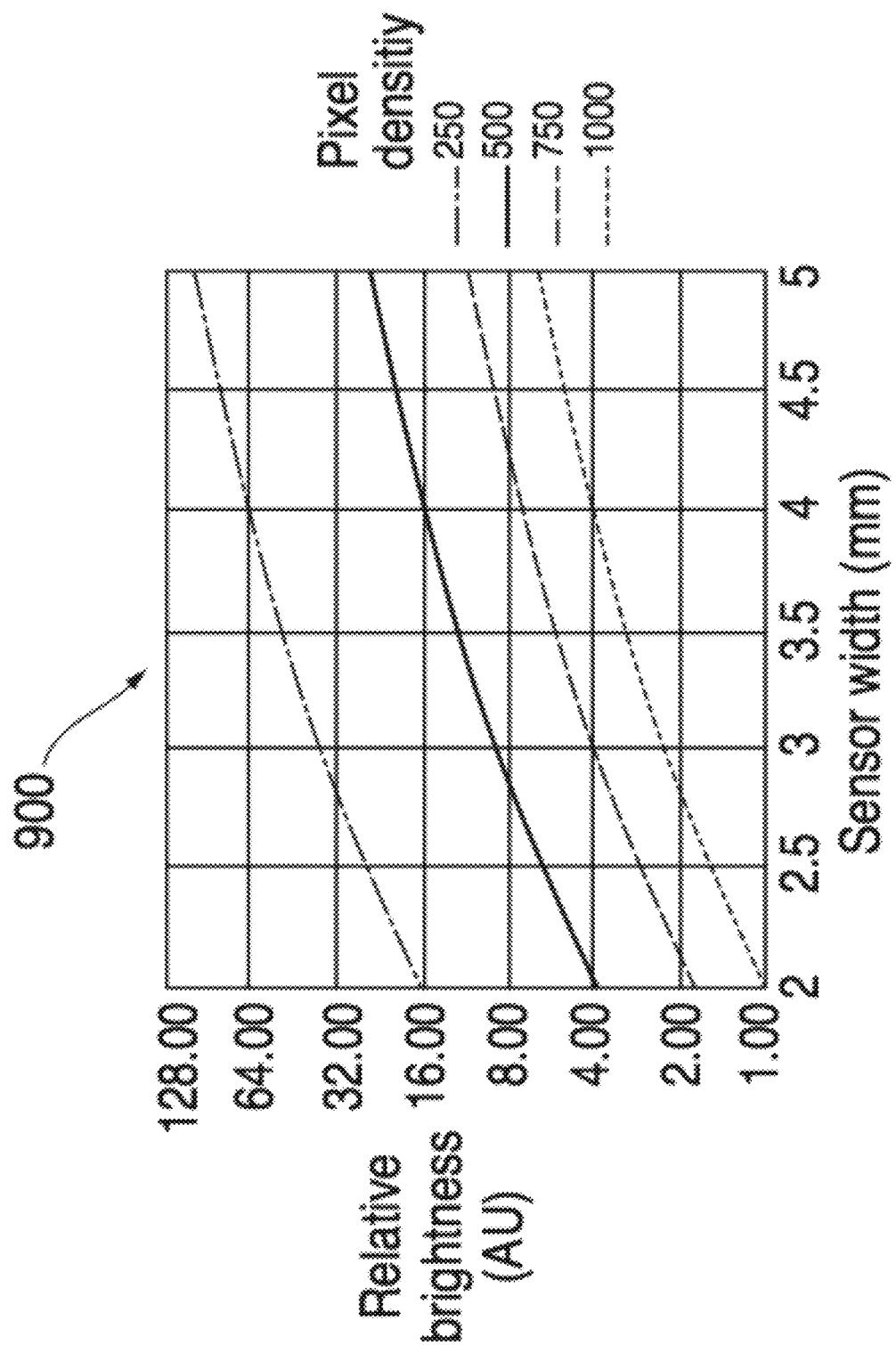
FIG. 9 is a representative plot of relative brightness versus sensor width for cameras with various pixel densities.

FIG. 9 is a representative plot 900 of relative brightness versus sensor width for cameras with various pixel densities. Referring to FIG. 9, increasing the pixel density of a sensor while holding constant the size of the sensor reduces the brightness of the image. For example, a sensor that is 4 mm wide with a pixel density of 500 has a relative brightness of 16 AU while a sensor that is 4 mm wide with a pixel density of 1,000 has a relative brightness of 4 AU.

Figure 10:
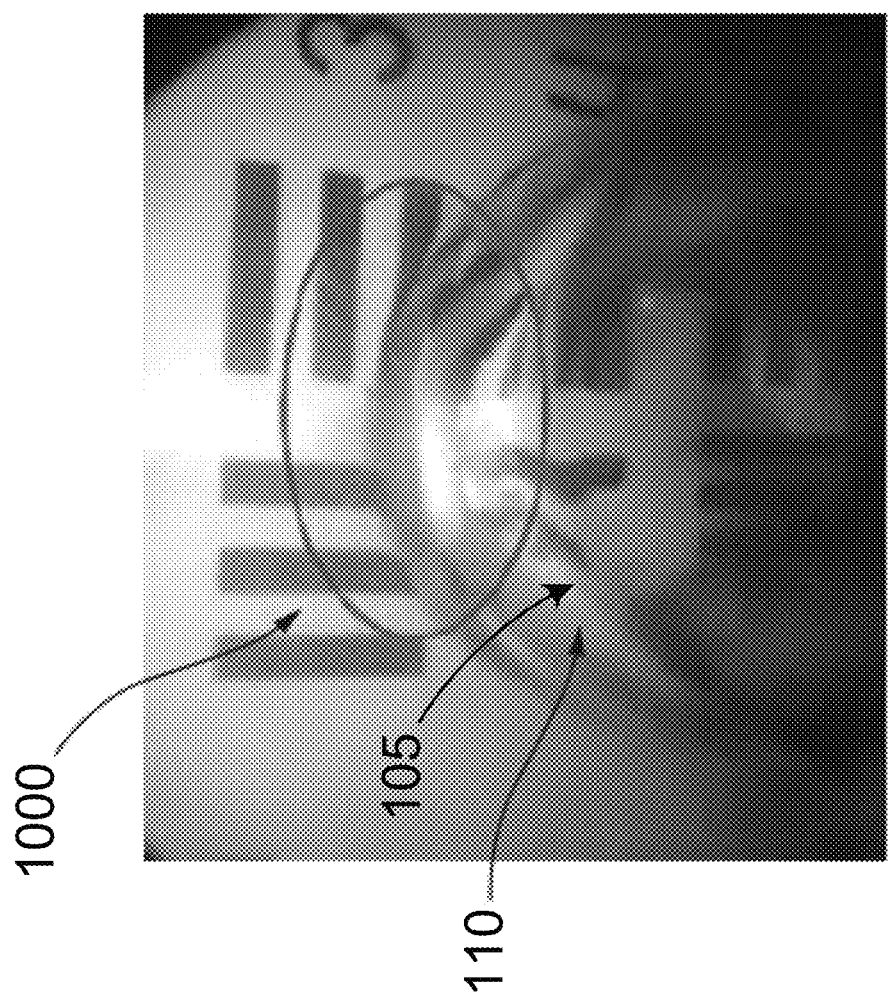
FIG. 10 is a representative illustration of distortion that can be caused by the bulb 110.

The bulb 110, 210, 310 (in general, bulb 110), described above can be designed to reduce image distortions caused by the presence of the bulb channel 105, 205, 305 (in general, bulb channel 105) or other features of the bulb 110 within the field of view of the imaging system 120, 320 (in general, imaging system 120). Image distortions can be created by features such as corners, bends, changes in thickness, changes in density, or other features of the bulb 110. Each of these features can act as a lens, creating a distortion in the images acquired by the imaging system 120. FIG. 10 is a representative illustration of a distortion that can be caused by the bulb 110. For instance, the bulb channel 105 is a clear cylinder that has edges and different optical properties than the bulk material of the bulb 110, and thus creates a lens effect 1000.

The effect of distorting features on the quality of the images acquired by the imaging system 120 can be reduced by the specific design of the geometry of the bulb. In some examples, distorting features can be positioned outside the field of view of the imaging system 120. For instance, the imaging system 120 and the bulb channel 105 can be positioned such that only a small portion of the bulb channel 105, or none at all, falls within the field of view of the imaging system 120. In some examples, features can be formed with a relatively large radius of curvature rather than with sharp edges or corners in order to mitigate the distorting effect of the features. For instance, features can be formed with a radius of curvature greater than 90 degrees, such as a radius of curvature of about 120 degrees to about 150 degrees. In some examples, the thickness of the bulb can be varied to compensate for distortions caused by features of the bulb 105. In some examples, the material or the refractive index of the bulb can be selectively altered in different locations to compensate for distortions.

Figure 11:
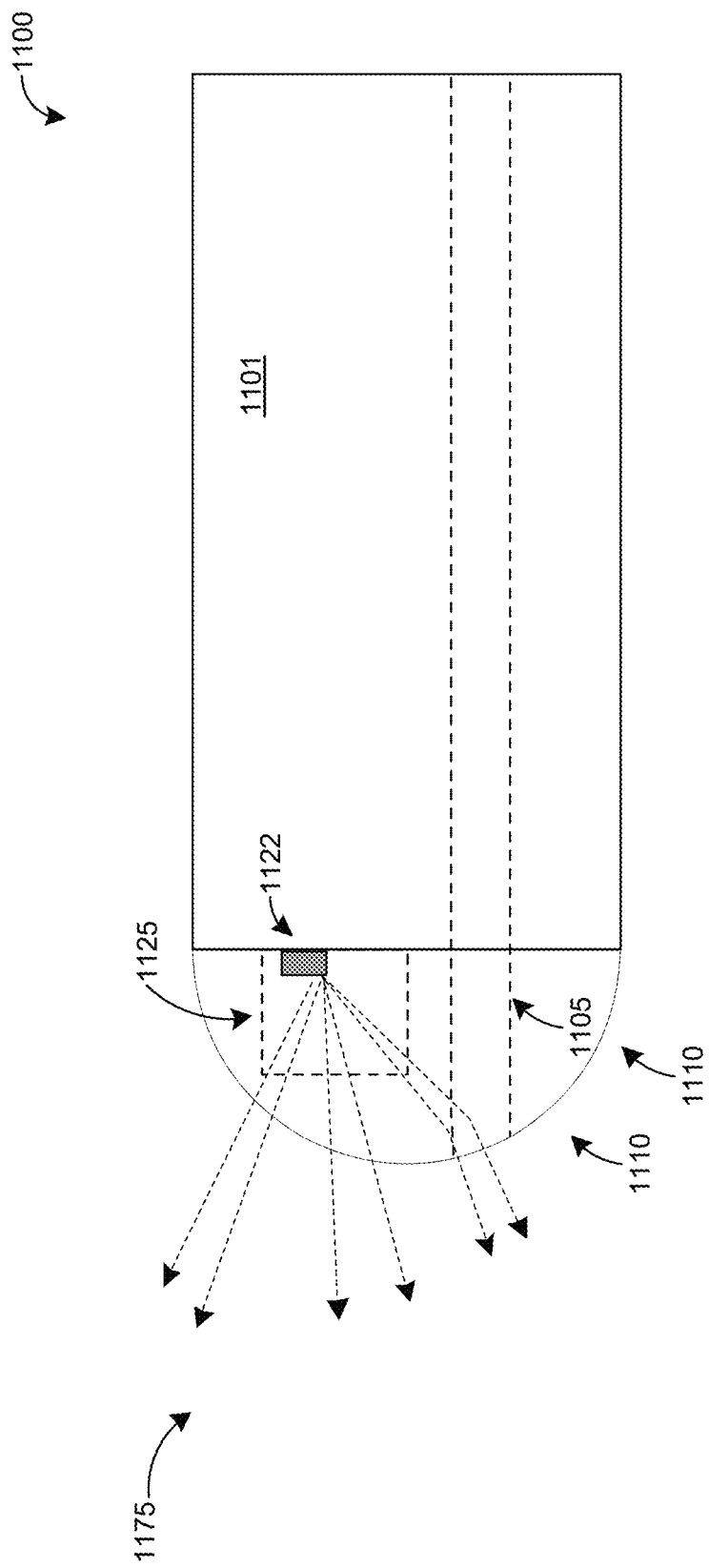
FIG. 11 illustrates an example of ray tracing of a hypothetical bulb that can be used to design the bulb for the instrument ports described herein.

FIG. 11 illustrates an example of ray tracing 1175 of a hypothetical bulb 1110 that can be used to design the bulb for the instrument ports described herein. Using ray tracing, the distortions caused by each feature of the bulb 1110, as light emitted from illumination source 1122 passes through, can be analyzed and corrected, if necessary. One example of a feature that may affect the path of the light include the interface between the hollow cavity 1125 and the bulb material. Another example of a feature that may affect the path of the light is bulb channel 1105 and its interface with the bulb material. Another example of a feature that may affect the path of the light is the interface between the bulb and the surrounding air (or body fluids).

For instance, a ray tracing analysis can be performed on a preliminary design for a bulb and the features causing distortions can be identified. The design of the bulb can be adjusted, for instance by changing the relative positions of the features of the bulb or changing the thickness of portions of the bulb. For example, the positions of the camera and illumination source within the bulb can be adjusted. The redesigned bulb can be analyzed again. The bulb design is thus iteratively updated until the distortions are minimized or until the effect of the distortions can be compensated for. The ray tracing can be performed using Zemax® (Zemax LLC, Kirkland, WA) non-sequential ray tracing.

In some examples, the distortions caused by features of the bulb can be quantitatively characterized, for instance, by ray tracing or another type of optical modeling. Then images acquired by the imaging system can be processed using software that takes into account the quantitative characterization of the distortions to remove the distortions from the images presented on a monitor to the user. In some examples, the ZeMax® Optic Studio (Zemax LLC, Kirkland, WA) can be used for image processing.

In some examples, the geometry of the bulb 110 can be optimized for use with a particular wavelength or range of wavelengths of light. The index of refraction of the bulb material and of blood are wavelength-dependent, and thus the distortions caused by the features of the bulb 110 or channel 105 can vary depending on the wavelength used by the imaging system. Thus, for instance, a bulb 110 designed to be used with infrared illumination can have a slightly different design than a bulb 110 designed to be used with visible light, such as a different positioning of the imaging system 120 or different local bulb thicknesses.

In some examples, the instrument ports described herein can be single-use, disposable surgical devices such that the instrument channel, the bulb channel, the inlet and outlet ports, and other components of the instrument channels do not need to be easily cleaned and sterilized for reuse. In some examples, the port body of an instrument port can be a reusable device and the bulb can be a single-use, disposable device that can be removably attached to the port body by a reversible closing mechanism, such as a pressure-fit seal, an O-ring attachment, or another closing mechanism. In some examples, the imaging system is embedded in the bulb and is disposable along with the bulb. In some examples, the imaging system is reusable and can be cleaned and sterilized and inserted into each disposable bulb.

The instrument ports described here can be used to perform cardiac procedures, such as beating heart cardiac procedures. Examples of cardiac procedures that can be carried out by the instrument ports described herein include closure of heart defects, such as septal defects, heart valve annuloplasty, and other procedures. The imaging capabilities provided by the instrument ports described here provide high quality imaging of the surgical procedure, thereby enabling complex surgical procedures to be carried out with a high degree of precision.

Figure 12:
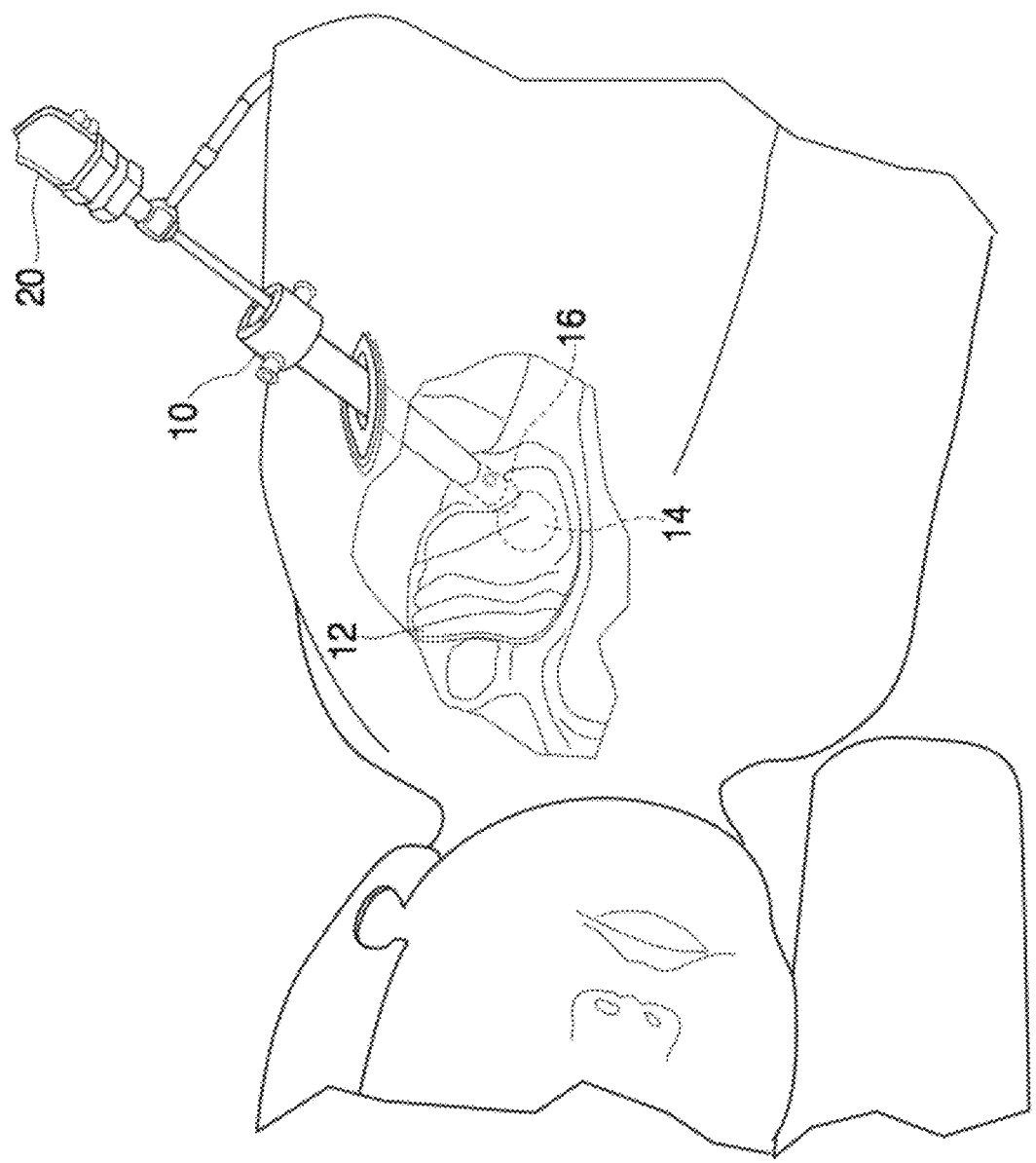
FIG. 12 is an illustration of a clinical use of an instrument port to perform a patent foramen ovale (PFO) closure procedure.

FIG. 12 is an illustration of a clinical use of instrument port 10 to perform a patent foramen ovale (PFO) closure procedure. In the PFO procedure, a patch is applied to the septum of a patient's heart 12 to close a hole 14 in the septum. In this procedure, an incision is made through the atrial or ventricular wall of the patient's heart and secured with a suture, such as a purse-string suture. The distal end of the instrument port 10 is inserted through the incision such that the distal face of the bulb 16 is positioned near or in contact with the septum of the patient's heart 12. The proximal end of the instrument port 10 remains outside the patient's body, enabling an operator of the instrument port 10 to adjust the position of the instrument port 10 and to manipulate an instrument 20 inserted into the instrument port 10. Once properly positioned, the instrument port 10 is secured in place, e.g., using the purse-string suture, to prevent blood leakage during the procedure.

While the drawings, e.g., FIG. 12, are intended to convey the general understanding of the configuration and use of the present systems, they are not intended to be strictly to scale or necessarily inclusive of the kinds of attachments and configurations comprehended by this disclosure. Those skilled in the art will appreciate that surgical endoscopic instrument uses and other uses are comprehended by certain aspects of the disclosure, as would be reasonable for a given situation.

A first instrument, such as graspers, scissors, a tissue anchor deployment device, a tissue stapler, a needle holder, or another type of instrument, is inserted through the instrument port to the surgical site and used to place the patch over the hole in the septum. The imaging system can image the first instrument as the instrument emerges from the bulb channel and manipulates the patch, providing valuable feedback to the operator of the instrument port about the condition of the patient's septum and the relative positions of the patch and the septum. Once the patch has been placed in the desired location, the first instrument is withdrawn and a second instrument, such as an anchor deployment device, a stapler, a needle holder (e.g., RD80), a suturing device (e.g., SR5 from LSI Solutions® LLC), or another type of instrument, is inserted through the instrument port to the surgical site. In an example, the present system and method may be used along with a tissue tacking system such as that disclosed in U.S. Pat. No. 8,491,631, or optically-guided surgical devices such as that disclosed in U.S. Pub. No. 2016/0367120 A1, which are incorporated herein by reference. The second instrument is used to anchor the patch onto the septum, e.g., by stitching the patch onto the septum, adhering the patch using a medical grade adhesive, or attaching the patch in another way. The imaging system can image the second instrument as the instrument emerges from the bulb channel and interacts with the patch, providing information to the operator of the instrument port about the relative positions of the patch and the instrument. Once the procedure is complete, the second instrument is withdrawn from the instrument port and the instrument port is withdrawn from the incision.

In some examples, when the instrument port has two instrument channels and two corresponding bulb channels, the first and second instruments can be inserted through the instrument port concurrently such that there is little delay between positioning the patch over the hole in the septum and anchoring the patch to the septum.

In an example, the instrument ports described herein can be used to apply and cure an activatable adhesive, such as a light-activated adhesive or a two-component chemically activated adhesive. A light-activated adhesive is an adhesive that undergoes an increase in adhesive properties responsive to application of light of a certain wavelength, such as ultraviolet light. An example of a light-activated adhesive is produced by Gecko Biomedical LLC (Paris, France). Light-activated adhesives can be used as a glue to bind to blood vessel walls or to heart tissue, acting as a biodegradable patch to temporarily close a hole or tear while tissue is regenerated to repair the hole.

In procedures to deliver and cure light-activated adhesives, the distal end of an instrument port is inserted through an incision such that the distal face of the bulb is positioned near or in contact with the tissue where the light-activated adhesive is to be applied. An instrument is inserted through the instrument port and used to apply the adhesive to the target tissue. The imaging system illuminates the surgical site with light of a wavelength that does not activate the adhesive, such as near-infrared light or long wavelength (e.g., red) visible light. Once the adhesive is applied to the target tissue, the instrument is withdrawn from the instrument port. The imaging system then illuminates the surgical site with light of a wavelength that will activate the adhesive, such as ultraviolet light or short wavelength (e.g., blue) visible light. Once the adhesive has been illuminated for a time sufficient to cause curing and adhesion, the instrument port is withdrawn from the surgical site.

In some examples, the imaging system can include two distinct illumination sources, one illumination source to provide red or near-infrared light and a second illumination source to provide blue or ultraviolet light. For instance, the imaging system can include multiple LEDs or multiple light guides. In some examples, the imaging system can include a single illumination source that provides red or near-infrared light. To provide ultraviolet illumination for activating the adhesive, an illumination source, such as an optical fiber, coupled to an ultraviolet light source can be inserted through the channels of the instrument port.

FIG. 13 is a flow chart 1300 of a method of introducing an instrument into a surgical site. In step 1310, an instrument port is placed into a surgical site. The instrument port can be the same or similar as the instrument ports described above. The instrument port includes a port body and a bulb disposed at a distal end of the port body. In step 1320, an instrument is inserted into a channel that extends from a proximal end to a distal end of the instrument port. The channel includes an instrument channel that extends through the port body and a bulb channel that extends through the bulb. In step 1330, one or more images of the surgical site and/or of the distal end of the instrument body is acquired using an imaging system disposed at the distal end of the instrument port. The imaging system is fluidically isolated from the surgical site and it includes a camera and an illumination source. In optional step 1340, the location of the instrument and/or the instrument port is adjusted based on the acquired image(s). In some embodiments, steps 1330 1340 are repeated until the instrument port is located at the desired location, for example relative to an anatomical feature.

In the foregoing specification, certain aspects have been described with reference to specific embodiments. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention.

What is claimed is:

1. An instrument port for introducing an instrument into a surgical site, the instrument port comprising:
   a port body having an instrument channel extending from a proximal end to a distal end of the port body;
   a bulb disposed at the distal end of the port body, the bulb comprising:

a transparent solid material filling a body of the bulb and defining a distal surface of the bulb, and a bulb channel extending from a proximal side to a distal side of the bulb, the bulb channel aligned with the instrument channel, wherein the bulb channel and instrument channel are configured to receive the instrument; and an imaging system disposed in a continuous hollow region defined in the solid material, wherein the imaging system comprises a camera and an illumination source, the illumination source configured to generate a light having a first wavelength, wherein the bulb is at least partially optically transparent to the first wavelength of the light, wherein the camera and the illumination source are each arranged in the continuous hollow region and are each spaced apart from the distal end of the port body, wherein the transparent solid material is arranged to laterally surround the continuous hollow region, wherein the transparent solid material is present in a common plane, orthogonal to a proximal-distal axis of the bulb, with the camera and the illumination source, and wherein:

the imaging system is fluidically isolated from the surgical site, a relative angle between a distal face of the bulb and a direction of illumination from the illumination source is configured to reduce internal reflections at the distal face of the bulb, and relative positions of the camera and the illumination source are configured to compensate for image distortion caused by refraction of light at an interface between the bulb channel and the transparent solid material that fills the body of the bulb.

2. The instrument port of claim 1, wherein the illumination source comprises a light guide configured to be optically coupled to a light source external to the instrument port.

3. The instrument port of claim 1, wherein the imaging system is fluidically isolated from the instrument channel and the bulb channel.

4. The instrument port of claim 1, wherein the continuous hollow region comprises a curved distal side defined by the transparent solid material.

5. The instrument port of claim 1, wherein the continuous hollow region is further defined by a bulb channel wall that defines the bulb channel.

6. The instrument port of claim 1, wherein the transparent solid material comprises silicone, polycarbonate, polypropylene, polyacetal, or polyether ether ketone, or a combination of two or more of the foregoing materials.

7. The instrument port of claim 1, wherein the imaging system is positioned such that a distal opening of the bulb channel falls within a field of view of the camera, and wherein the bulb does not include features obstructing the field of view of the camera.

8. The instrument port of claim 1, wherein the bulb is attached to the port body by a fluid-tight seal.

9. The instrument port of claim 1, wherein a refractive index of the bulb is varied at different locations to compensate for distortions of images acquired by the camera.

10. The instrument port of claim 1, wherein a geometry of the bulb is optimized for use with a particular wavelength of light.

11. The instrument port of claim 1, wherein the imaging system is inset from an external surface of the bulb by a range of about 0.5 mm to about 1.5 mm.

12. The instrument port of claim 1, wherein the imaging system is inset from the distal face of the bulb by a focal distance of the camera.

13. The instrument port of claim 1, wherein the bulb is hemispherically-shaped.

14. The instrument port of claim 1, wherein the transparent solid material comprises a deformable material that conforms to a shape of tissue at the surgical site.

15. The instrument port of claim 1, wherein the bulb comprises a material having a refractive index that reduces the internal reflections at the distal face of the bulb.

16. The instrument port of claim 1, wherein a rounded portion of the bulb has a degree of curvature between 120 degrees and 150 degrees.

17. The instrument port of claim 1, comprising an anti-reflective coating on an inner surface of the bulb.

18. The instrument port of claim 1, wherein a lateral separation between the imaging system and the instrument channel is between 0.1 mm and 0.5 mm.

19. The instrument port of claim 1, wherein the camera and the illumination source are disposed on a pedestal or a post that extends from the distal end of the port body.

20. The instrument port of claim 1, wherein the bulb comprises a collar arranged at the proximal side of the bulb and configured to engage with the distal end of the port body to form a fluid-tight seal between the bulb and the port body.

21. The instrument port of claim 20, wherein the collar has a larger lateral dimension than a lateral dimension of the distal end of the port body.

22. The instrument port of claim 20, wherein the interface between the bulb channel and the transparent solid material that fills the body is an interface between a hollow space of the bulb channel and the transparent solid material that fills the body.

* * * * *